(12) United States Patent
Bao et al.

(10) Patent No.: US 6,251,601 B1
(45) Date of Patent: Jun. 26, 2001

(54) SIMULTANEOUS MEASUREMENT OF GENE EXPRESSION AND GENOMIC ABNORMALITIES USING NUCLEIC ACID MICROARRAYS

(75) Inventors: Yijia Bao, Naperville; Diping Che, Westmont; Wan-Liang Li, Lisle; Uwe Richard Müller, Plano; Steven A. Seelig, Naperville; Jufang Shi, Hinsdale, all of IL (US)

(73) Assignee: Vysis, Inc., Downers Grove, IL (US)

( * ) Notice: Subject to any disclaimer, the term of this patent is extended or adjusted under 35 U.S.C. 154(b) by 0 days.

(21) Appl. No.: 09/243,067

(22) Filed: Feb. 2, 1999

(51) Int. Cl.[7] ............................................. C12Q 1/68

(52) U.S. Cl. .................. 435/6; 536/26.6; 422/50; 422/52; 422/55; 422/56; 422/57; 435/69.1; 435/320.1

(58) Field of Search ................... 435/6, 69.1, 320.1; 536/26.6; 422/50, 52, 55, 56, 57

(56) References Cited

U.S. PATENT DOCUMENTS

| | | | |
|---|---|---|---|
| 5,807,522 | * | 9/1998 | Brown et al. ............... 422/50 |
| 5,972,606 | * | 10/1999 | Creasy et al. ............... 435/6 |
| 6,044,755 | * | 10/1999 | Wang ............................ 435/6 |

* cited by examiner

*Primary Examiner*—W. Gary Jones
*Assistant Examiner*—Janell Taylor
(74) *Attorney, Agent, or Firm*—William E. Murray

(57) ABSTRACT

The invention comprises a multi-color, comparative hybridization assay method using an array of nucleic acid target elements attached to a solid support for the simultaneous detection of both gene expression and chromosomal abnormalities in a tissue sample. The method of the invention employs a comparative hybridization of a tissue mRNA or cDNA sample labeled in a first fluorescent color, a tissue chromosomal DNA sample labeled in a second fluorescent color, and at least one reference nucleic acid labeled in a third fluorescent color, to the array. The fluorescent color presence and intensity at each of at least two target elements are detected and the fluorescent ratios (i) of the first and third colors and (ii) the second and third colors determined. Gene expression and chromosomal abnormalities are thus simultaneously detected.

78 Claims, 8 Drawing Sheets

TOP VIEW

SIDE VIEW

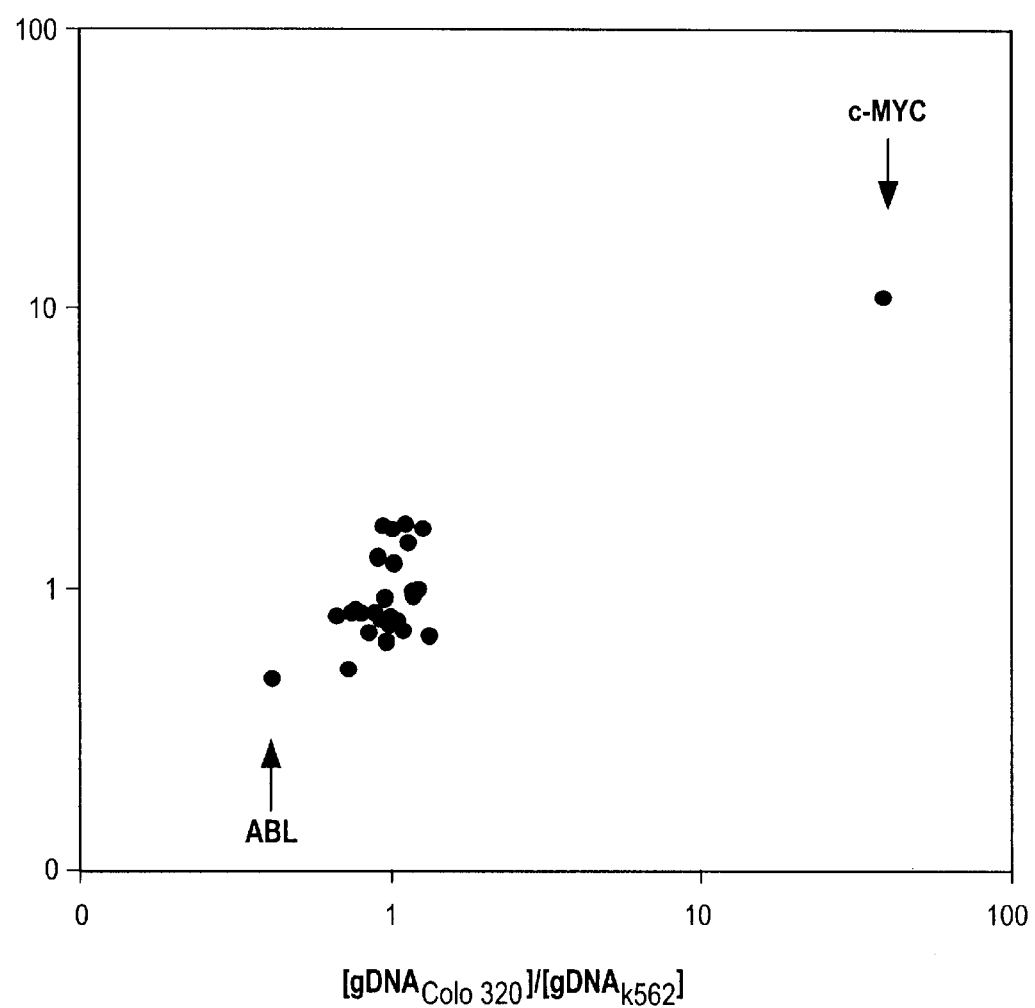

SIMULTANEOUS MEASUREMENT OF GENE EXPRESSION AND GENOMIC ABNORMALITIES USING NUCLEIC ACID MICROARRAYS

GOVERNMENT RIGHTS

The United States has certain rights in this invention pursuant to a grant for ATP Project No. 94-05-0021, Award No. 70NANB5H1108 from the National Institute of Standards and Technology.

FIELD OF THE INVENTION

This invention relates generally to the assessment of nucleic acids in human or animal tissue samples. More particularly, the invention relates to the simultaneous measurement in tissue samples of gene expression and of chromosome abnormalities.

BACKGROUND OF THE INVENTION

Abnormalities in the expression of genes, both in the timing and level of expression of particular genes, are a fundamental cause of cancer and other human disease. Abnormalities in genomic DNA, i.e. in chromosomes, are also a fundamental cause of cancer and other human disease, often leading to the over-expression or under-expression of genes. Some chromosomal abnormalities, such as balanced translocations and inversions between chromosomes, and base pair changes, do not involve a change in DNA sequence copy number. Other genomic DNA abnormalities comprise changes in DNA sequence copy number from the normal one copy per chromosome. These genomic DNA abnormalities often are referred to as gene amplification for copy number increase and gene deletion for copy number decrease. For example, one aggressive form of breast cancer, occurring in about 25–30% of breast cancers, results from the gene amplification and over-expression of the Her-2/neu oncogene, which is located on chromosome 17 at band q12. Breast cancer patients with this genetic abnormality have a significantly poorer prognosis, both for overall survival and disease-free survival, then patients without this abnormality. In addition, over-expression of the Her-2 gene occurs, in the absence of gene amplification of the chromosomal locus of the gene, at an earlier, less aggressive stage of the disease, Borg, et al., "Her-2/neu Activity in Human Breast Cancer," Cancer Research 50, 4332–4337 (Jul. 15, 1990). Proper assessment and management of breast cancer thus requires tests to measure the presence of Her-2 gene expression and Her-2 gene chromosomal copy number.

Chromosomal abnormalities such as Her-2 gene copy number can be assessed by assays using fluorescent in situ hybridization ("FISH"). FISH assays involve hybridization of DNA probes to chromosomal DNA present in morphologically intact metaphase spreads or interphase cells of tissue samples.

The U.S. Food and Drug Administration recently approved a diagnostic FISH test, PathVysion™ Her-2, available from Vysis, Inc. (Downers Grove, Ill.) for detection of Her-2 copy number and prediction of outcome of adriamycin therapy in node positive breast cancer patients.

Cancer also involves abnormalities in multiple genes, leading to multiple forms of the disease, as exemplified by breast cancer, wherein the Her-2 oncogere is not abnormal in the majority of cases. So-called "DNA Chip" or "microarray" tests using hybridization to a two dimensional array of multiple nucleic acid probes attached to a solid substrate assess multiple gene expression abnormalities simultaneously. See for example, U.S. Pat. Nos. 5,445,934, "Array of Oligonucleotides on Solid Substrate," Fodor, et al., 5,800,992, "Method of Detecting Nucleic Acids," Fodor, et al., and 5,807,552, "Methods for Fabricating Microarrays of Biological Substances," Brown, et al. The microarray gene expression tests are of growing use in the development of new drugs targeted at particular diseases.

Multiple gene expression at the protein level also can be examined by the use of "microdot" immunoassays, which are two dimensional arrays of immobilized antigens on a substrate. See U.S. Pat. No. 5,486,452, "Devices and Kits for Immunological Analysis," Gordon, et al., priority date Feb. 3, 1982, and Ekins, et al, Analytica Chimica Acta, 227:73–96 (1989). The immobilized antigens of Gordon, et al. include nucleic acids and are disclosed as arrayed at densities of $10^5$ per 10 square centimeters (or 1,000 per $cm^2$). Gordon, et al. further disclose the array has "intrinsic resolution" below the size of pipetting devices common in 1982, see Gordon, et al. at column 17, and can thus contain antigens at higher densities. Gordon, et al. disclose that the arrays can be manufactured by use of mechanical transfer apparatus, miniaturized applicators, lithographic procedures or high speed electronic printing.

U.S. Pat. No. 5,665,549, "Comparative Genomic Hybridization (CGH)," Pinkel, et al., discloses a method for simultaneous assessment of multiple genetic abnormalities. CGH involves the comparative, multi-color hybridization of a reference nucleic acid population labeled in one fluorescent color and a sample nucleic acid population labeled in a second fluorescent color to all or part of a reference genome, such as a human metaphase chromosome spread. Comparison of the resulting fluorescence intensity at locations in the reference genome permits determination of copy number of chromosomal sequences, or of expressed gene sequences, in the sample population. Microarray-based CGH tests have also been disclosed for the assessment of multiple genomic DNA or gene expression abnormalities, see U.S. Pat. No. 5,830,645, "Comparative Fluorescent Hybridization to Nucleic Acid Arrays, Pinkel, et al.; co-pending and commonly assigned U.S. patent application Ser. No. 09/085,625, "Improvements of Biological Assays for Analyte Detection," Muller, et al.; and Pinkel, et al., "High resolution analysis of DNA copy number variation using comparative genomic hybridization to microarrays," Nature Genetics, Vol. 20, October 1998, pp. 207–211. Pinkel, et al. in Nature Genetics disclose the capability of CGH to a microarray target to detect a single copy change in genomic DNA.

To date, assessment of gene expression and of chromosomal abnormalities requires separate tests on a tissue sample, leading to extra sample processing and reagent costs. Separate testing for gene expression and chromosomal abnormalities can also require more tissue than is available. The prior art does not disclose simultaneous measurement of gene expression and chromosomal abnormalities with a multi-color hybridization to a microarray. It is an object of this invention to circumvent separate testing by performing simultaneous testing for gene expression and chromosomal abnormalities on a tissue sample. It is another object to simultaneously test gene expression and chromosomal abnormalities on a single nucleic acid microarray. Other objects of the invention will be detailed below.

SUMMARY OF THE INVENTION

The invention comprises a multi-color, comparative hybridization assay method using an array of nucleic acid target elements attached to a solid support for the simultaneous detection of both gene expression and chromosomal abnormalities in a tissue sample. The method of the invention employs a comparative hybridization of a tissue mRNA or cDNA sample labeled with a first detectable marker, a tissue genomic DNA sample labeled with a second detectable marker, and at least one reference nucleic acid labeled with a third detectable marker, to the array. Each marker's presence and intensity at each target element is detected and the ratios of the markers, for example, (1) of the first and third markers and (2) the second and third markers, are determined for each of the target elements. Gene expression and chromosomal abnormalities are thus simultaneously detected by analysis of the marker ratios. In a preferred embodiment, the markers are each fluorescent labels.

The invention has broad utility in human disease management by providing more complete genetic assessment data to guide therapy selection, in human and animal drug development programs by assessing therapeutic candidate effects, and in bacterial and viral pathogen diagnosis. Particular cancers, which are characterized by gene amplification coupled with over-expression of the mRNA for the amplified gene, may be more aggressive diseases and need more aggressive therapies. The mechanism that drives over-expression could be fundamental in understanding what therapeutic interventions may be appropriate. Thus, the characterization of both gene expression and amplification by the methods of the invention can lead to improved cancer therapy.

In a preferred embodiment, the invention comprises a method for simultaneous detection of gene expression and chromosomal abnormality in a tissue sample comprising:

(a) providing a microarray of nucleic acid target elements attached to a solid support wherein the nucleic acid target elements comprise polynucleotide sequences substantially complementary under preselected hybridization conditions to nucleic acids present in a tissue sample, which are indicative of gene expression and indicative of chromosomal sequence;

(b) providing at least three labeled probe nucleic acid populations:

(i) a cDNA population labeled in a first fluorescent color and derived from mRNA from the tissue sample, (ii) a chromosomal DNA population labeled in a second fluorescent color and derived from the tissue sample, and (iii) at least one reference nucleic acid population labeled in a third fluorescent color;

(c) contacting the microarray with the labeled nucleic acid populations under hybridization conditions; and (d) detecting presence and intensity of each of the first, second and third fluorescent label colors on at least two target elements.

Measurement and comparison of hybridization of message, genomic and reference nucleic acids at the same target elements provides the simultaneous assessment of expression and genomic changes. The invention also comprises use of multiple reference nucleic acids, for example, a genomic reference DNA labeled in the third fluorescent color and a reference cDNA population labeled in a fourth fluorescent color. The nucleic acid target elements can be either genomic DNA, oligomer DNA or cDNA. A preferred embodiment comprises an array with a mixture of genomic DNA target elements and oligomer DNA or cDNA target elements, with the oligomer DNA/cDNA targets measuring expression and the genomic DNA targets measuring chromosomal change. It is also preferred to use a microarray having a target element density capable of measuring 1,000 different gene and genomic loci in less than one square centimeter of chip surface.

Figure 1A:
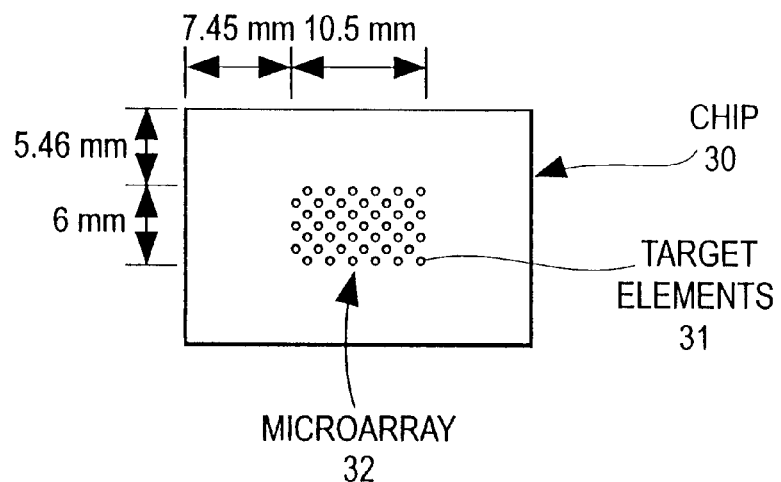
FIGS. 1 (*a*) through 1 (*e*) depict the components of a preferred hybridization cartridge for use in performing the inventive methods.
Figure 1B:
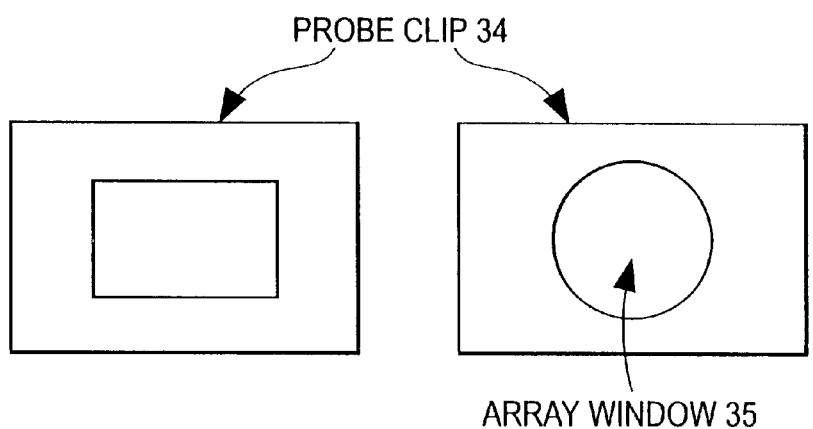
Figure 1C:
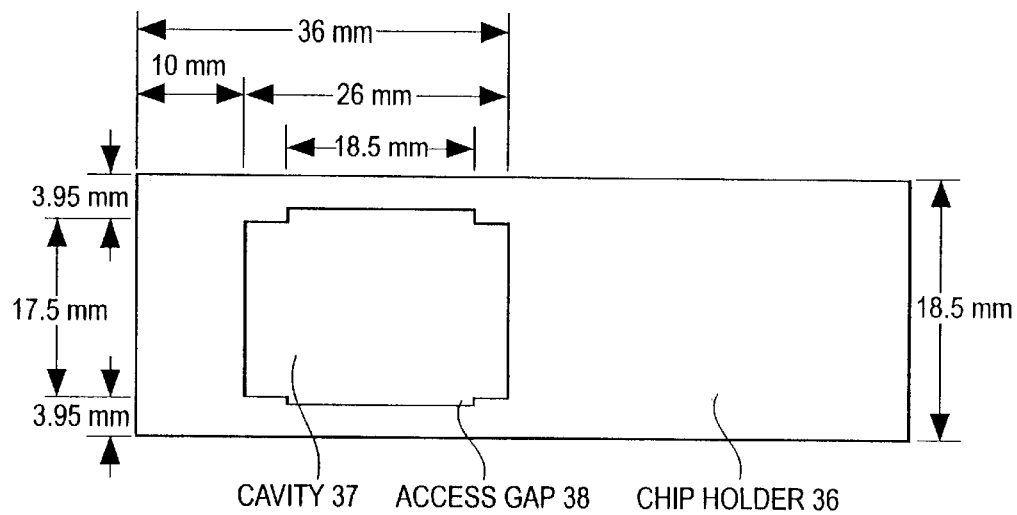
Figure 1D:
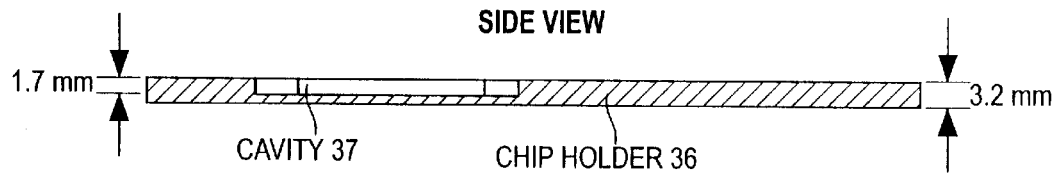
Figure 1E:
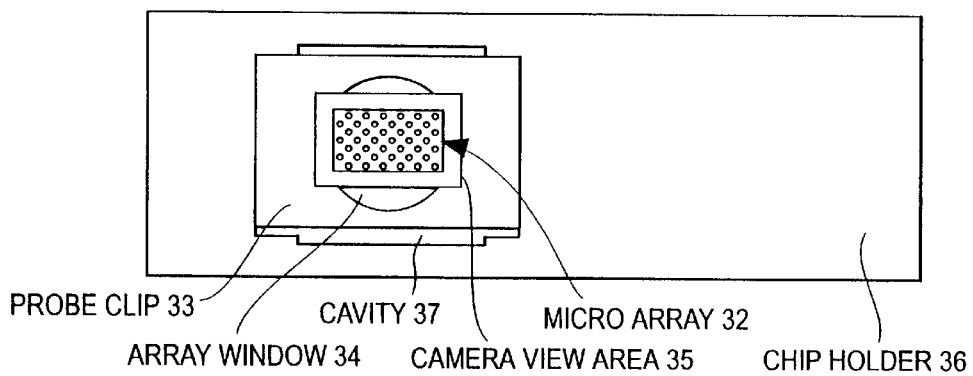

DETAILED DESCRIPTION OF THE INVENTION (1) Definitions

The following abbreviations are used herein:

bp—base pair

CGH—Comparative Genomic Hybridization

DAPI—4, 6 diamidino-2-phenylindole dCTP—deoxycytosine triphosphate

DNA—deoxyribonucleic acid (in either single- or double-stranded form, including analogs that can function in a similar manner)

dUTP—deoxyuridine triphosphate

FISH—fluorescence in situ hybridization kb—kilobase mm—millimeter mRNA—messenger RNA ng—nanogram nl—nanoliter RNA—ribonucleic acid in either single- or double-stranded form, including analogs that can function in a similar manner $\mu$g—microgram $\mu$l—microliter $\mu$m—micrometer $\mu$M—micromole The term "nucleic acid" or "nucleic acid molecule" refer to a deoxyribonucleotide or ribonucleotide polymer in either single- or double-stranded form, including known analogs of natural nucleotides that can function in a similar manner as naturally occurring nucleotides.

The term "exon" refers to any segment of an interrupted gene that is represented in the mature mRNA product. Some protein coding genes do have exons that are non-coding, e.g., exon 1 of the human c-myc gene. Perhaps all protein coding genes have first and last exons that are partially coding.

The terms "single copy sequence" or "unique sequence" refer to a nucleic acid sequence that is typically present only once per haploid genome, such as the coding exon sequences of a gene.

The term "complexity" is used herein according to standard meaning of this term as established by Britten, et al., *Methods of Enzymol.*, 29:363 (1974). See also Cantor and Schimmel, *Biophysical Chemistry: Part III* at 1228–1230, for further explanation of nucleic acid complexity.

The term "target element" refers to a region of a substrate surface that contains immobilized or attached nucleic acids capable of hybridization to nucleic acids isolated from a tissue sample. "Bind(s) substantially" refers to complementary hybridization between a tissue nucleic acid and a target element nucleic acid and embraces minor mismatches that can be accommodated by reducing the stringency of the hybridization media to achieve the desired detection of the tissue polynucleotide sequence.

The terms "specific hybridization" or "specifically hybridizes with" refers to hybridization in which a tissue nucleic acid binds substantially to target element nucleic acid and does not bind substantially to other nucleic acids in the array under defined stringency conditions. One of skill will recognize that relaxing the stringency of the hybridizing conditions will allow sequence mismatches to be tolerated. The degree of mismatch tolerated can be controlled by suitable adjustment of the hybridization conditions.

One of skill will also recognize that the precise sequence of the particular nucleic acids described herein can be modified to a certain degree to produce tissue nucleic acid probes or target element nucleic acids that are "substantially identical" to others, and retain the ability to bind substantially to a complementary nucleic acid. Such modifications are specifically covered by reference to individual sequences herein. The term "substantial identity" of polynucleotide sequences means that a polynucleotide comprises a sequence that has at least 90% sequence identity, and more preferably at least 95%, compared to a reference sequence using the methods described below using standard parameters.

Two nucleic acid sequences are said to be "identical" if the sequence of nucleotides in the two sequences is the same when aligned for maximum correspondence as described below. The term "complementary to" is used herein to mean that the complementary sequence is complementary to all or a portion of a reference polynucleotide sequence.

Sequence comparisons between two (or more) polynucleotides are typically performed by comparing sequences of the two sequences over a "comparison window" to identify and compare local regions of sequence similarity. A "comparison window," as used herein, refers to a segment of at least about 20 contiguous positions, usually about 50 to about 200, more usually about 100 to 150, in which a sequence may be compared to a reference sequence of the same number of contiguous positions after the two sequences are optimally aligned.

Optimal alignment of sequences for comparison may be conducted by the local homology algorithm of Smith and Waterman, *Adv. Appl Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci. (U.S.A.)* 85:2444 (1988), and by computerized implementations of these algorithms.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

Another indication that nucleotide sequences are substantially identical is if two molecules hybridize to the same sequence under stringent conditions. Stringent conditions are sequence dependent and will be different in different circumstances. Generally, stringent conditions are selected to be about 50° to about 250° C. lower than the thermal melting point (Tm) for the specific sequence at a defined ionic strength and pH. The Tm is the temperature (under defined ionic strength and pH) at which the strands of a DNA duplex or RNA-DNA hybrid are half dissociated or denatured.

As used herein, a "probe" is defined as a population or collection of tissue nucleic acid molecules (either RNA or DNA) capable of binding to a target element comprising nucleic acid of complementary sequence through one or more types of chemical bonds, usually through hydrogen bond formation. The probe populations are directly or indirectly labeled as described below. The probe populations are typically of high complexity, for instance, being prepared from total genomic DNA or total mRNA isolated from a tissue cell or tissue cell population.

(2) Overview

The methods of the invention combine the capability of assessment of a large number of nucleic acids provided by microarray test formats with the multi-color, comparative hybridization power of CGH to assess simultaneously both gene expression and genomic abnormalities in the same tissue sample. The methods of the invention employ hybridization under suitable hybridization conditions to a nucleic acid array comprising multiple nucleic acid target elements of nucleic acid populations derived from a tissue sample. The nucleic acid target elements comprise either genomic DNA, oligomer or cDNA nucleic acids complementary to expressed gene sequences, or a mixture of the two. The nucleic acid populations are separately labeled with different detectable markers and comprise (1) a mixture of mRNA or its complementary cDNA, which is representative of gene expression in the tissue sample, and (2) a mixture of genomic DNA, which is representative of the genomic status of the tissue sample. The labeled nucleic acid populations are co-hybridized to the array with one or more reference nucleic acid populations, with each reference population also labeled with its own different detectable marker. Preferably, all of the nucleic acid populations applied to the array are each labeled with different fluorescent markers. The reference nucleic acid or nucleic acids is or are chosen to permit assessment of the gene expression state and genomic state of the tissue sample relative to the reference or references. After a suitable hybridization time, the fluorescent color presence and intensity are detected at each target element of the array. Comparison of the fluorescent ratios between colors at a particular target element provides measurement of the copy number for genomic DNA sequences and for cDNA sequences, which are complementary to that target element.

A genomic DNA sequence generally contains both one or more "exon" sequences, which code for all or part of the RNA expressed gene sequence, and one or more "intron," non-coding sequences, which also often contain repeat sequences replicated at many points in the human genome. A genomic target element can thus serve as a hybridization target for the expressed gene sequences that map to the particular genomic sequence. Similarly, a target element complementary to a particular expressed gene sequence is also complementary to the exon sequences of genomic DNA. Hence, a genomic DNA target element and a cDNA target element can each be used in an array format for hybridization to either genomic DNA or expressed gene sequence nucleic acids. The array format used in the methods of the invention comprises a microarray of separate nucleic acid target elements each complementary to (1) a particular genomic DNA sequence or (2) a particular expressed gene sequence. A mixture of target elements comprising some target elements complementary to (1) and some complementary to (2) can also be used.

A significant advantage of the methods of the invention is the simultaneous determination of both gene expression and chromosomal abnormality. Some aggressive, virulent forms of cancer are characterized by both over-expression of one or more oncogenes and gene amplification of the chromosomal locus of each oncogene, such as breast cancer involving Her-2. Testing for over-expression of the oncogene alone is inadequate for the complete characterization of the disease state. Simultaneous testing of the same tissue sample for both gene expression and chromosomal abnormalities with the methods of the invention thus advantageously identifies both over-expression and the molecular causes of over-expression and thereby enables appropriate prognostic assessment and therapy selection.

The choice of genomic, cDNA or a mixture of target elements can vary with the tissue and analysis sought. For example, cDNA target elements are advantageous because the effect of repeat sequences present in some genomic DNAs is decreased and more precise detection of expressed genes is possible. Genomic DNA target elements are advantageous because the higher complexities can produce greater signal. A mixture of genomic DNA and cDNA target elements can also be used to provide more detailed genomic and expression analysis.

(3) Nucleic Acids in the Target Elements

The nucleic acid sequences of the target elements can comprise any type of nucleic acid or nucleic acid analog, including without limitation, RNA, DNA, peptide nucleic acids or mixtures thereof, and can be present as clones also comprising vector sequences or can be substantially pure. Arrays comprising peptide nucleic acids are disclosed in U.S. Pat. No. 5,821,060, "DNA Sequencing, Mapping and Diagnostic Procedures Using Hybridization Chips and Unlabeled DNA," H. Arlinghaus, et al.

The nucleic acids of a target element typically have their origin in a defined region of a selected genome (for example a clone or several contiguous clones from a human or animal genomic library), or correspond to a functional genetic unit of a selected genome, which may or may not be complete (for example a full or partial cDNA sequence). The target nucleic acids can also comprise inter-Alu or Degenerate Oligonucleotide Primer PCR products derived from cloned DNA.

The nucleic acids of a target element can, for example, contain specific genes or be from a chromosomal region suspected of being present at increased or decreased copy number in cells of interest, e.g., tumor cells. For example, separate target elements can comprise DNA complementary to each of the oncogene loci listed in Table 2 below. The target element may also contain an mRNA or cDNA derived from such mRNA, suspected of being transcribed at abnormal levels, for example, expressed genes mapping to the gene loci in Table 2 below.

Alternatively, a target element may comprise nucleic acids of unknown significance or location. An array of such elements could represent locations that sample, either continuously or at discrete points, any desired portion of a genome, including, but not limited to, an entire genome, a single chromosome, or a portion of a chromosome. The number of target elements and the complexity of the nucleic acids in each would determine the density of analysis. For example, an array of 300 target elements, with each target containing DNA from a different genomic clone, could sample, i.e., analyze, the entire human genome at 10 megabase intervals. An array of 3,000 target elements, with each containing 100 kb of genomic DNA, could give substantially complete coverage at one megabase intervals of the unique sequence regions of the human genome. Similarly, an array of target elements comprising nucleic acids from anonymous cDNA clones or complementary to Expressed Sequence Tags ("ESTs") would permit identification of those expressed gene sequences that might be differently expressed in some cells of interest, thereby focusing attention on study of these genes or identification of expression abnormalities for diagnosis.

One of skill will recognize that each target element can comprise a mixture of target nucleic acids of different lengths and sequences. A target element will generally contain more than one copy of a cloned or synthesized piece of DNA, and each copy can be broken into fragments of different lengths. The length and complexity of the target element sequences of the invention is not critical to the invention. One of skill can adjust these factors to provide optimum hybridization and signal production for a given hybridization procedure, and to provide the required resolution among different genes or genomic locations.

The target elements can comprise oligomers, such as those in the range of 8 to about 100 bp, preferably 20 to 80 bp, and more preferably about 40 to about 60 bp, which can be readily synthesized using widely available synthesizer machines. Oligomers in target elements can also be synthesized in situ on the array substrate by any methods, such as those known in the art. The oligomer sequence information can be obtained from any convenient source, including nucleic acid sequence data banks, such as GENBANK, commercial databases such as LIFESEQ from Incyte Pharmaceuticals, Inc. (Palo Alto, Calif.), or EST data such as that produced by use of SAGE (serial analysis of gene expression). For oligomer or partial cDNA elements, one need only synthesize a partial sequence complementary to a part of the mRNA for the gene or complementary to an identifiable, critical sequence for the gene (critical in the sense of the sequences coding for the functional parts of the expressed protein, i.e., of the receptor binding site).

The target elements can comprise partial or full-length cDNA sequences, either synthesized for smaller cDNAs or cloned, preferably having a complexity in the range of about 100 bp to about 5,000 bp. cDNA target elements can be readily obtained from expressed gene sequence cDNA libraries from a desired tissue, which are produced using conventional methods or obtained from commercial sources, such as the libraries maintained by Genome Systems, Inc. (St. Louis, Mo.), Research Genetics (Huntsville, Ala.) and Clonetech (South San Francisco, Calif.).

The target elements can comprise genomic DNA sequences of any complexity, but generally of a complexity of about 20,000 bp to about 250,000 bp, and preferably about 50,000 bp to about 175,000 bp. Genomic DNA can be obtained from any mapped genomic clones produced by standard cloning procedures or obtained from commercial sources, such as the chromosome specific libraries maintained by the American Type Culture Collection (Rockville, Md.), hereinafter ATCC. A preferred genomic library source is the human DNA BAC library maintained by Genome Systems.

The identification of genomic DNA or cDNA selected for use in the target elements can be determined by the location of chromosomal sequences known or identified as amplified or deleted or of genes over- or under-expressed. The identification of genomic or cDNA clones is done by designing primer sequence pairs using, for example, genetic data in Gene Map '98 maintained by the U. S. National Institute of Health or the Genome Data Base at htttD://adbwww.gdb.org/gdbtop.html. For example, the Her-2 gene is believed to comprise about 40 kb of genomic sequence and a PCR primer pair can be designed based upon the published Her-2 sequence. The PCR primer pair or the PCR amplicon product can then be used to screen a genomic DNA library to identify clones containing complementary sequences. The genomic DNA clones identified in the screen can be used on an array in the method of the invention to identify genomic abnormality at the Her-2 locus.

For use of arrays that detect viruses and viral gene expression simultaneously with detection of human genetic abnormalities, the target elements can comprise sequences complementary to known or identified viral sequences. The array target elements can also be designed to detect viral integration sites in the human or an animal genome. Use of such a pathogen array is medically significant, for example, because of the known ties of human papilloma virus to human cervical cancer and h. pylori to human gastrointestinal cancer. Similarly, known bacterial gene sequences can be used to design the nucleic acids of the target elements. Use of pathogen sequence based arrays also can be used in food and environmental testing.

(4) Target Elements

The target elements can be of varying dimension, shape and area. The target elements can comprise physically separated spots produced by printing methods, for example, mechanical transfer, gravure, ink jet or imprint methods. The target elements also can be closely abutted such as those produced by the photolithographic in situ array synthesis of U.S. Pat. No. 5,445,934. The target elements are preferably generally round in shape on a planar surface. Generally, smaller elements are preferred, with a typical target element comprising less than 500 microns in diameter. Particularly preferred target element sizes are between about 5 microns and 250 microns in diameter to achieve high density.

The target element density can be any desired density and is preferably one typical of nucleic acid microarrays, i.e. greater than about 100 target elements per square centimeter. For the preferred use in human disease management, the target element density is preferably in the range of about 100 to about 10,000 target elements per square centimeter of chip surface. Higher or lower densities can be desirable and higher densities can be preferred for use in drug development to permit examination of higher numbers of expressed gene sequences.

(5) Array Manufacture

The microarray can be manufactured in any desired manner and both robotic deposition and synthesis in situ methods for array manufacturing are known. See for example, U.S. Pat. Nos. 5,486,452, 5,830,645, 5,807,552, 5,800,992 and 5,445,934. It is preferred to manufacture the microarray using a robotic deposition method and apparatus, which employs robotic deposition of nucleic acids through a capillary needle or pin as disclosed in co-pending, commonly assigned U.S. patent application Ser. No. 09/085,625, filed May 27, 1998, "Improvements of Biological Assays for Analyte Detection," Muller, et al. (hereinafter "Muller, et al."), to produce a two dimensional microarray of physically separated or "spotted" target elements immobilized in rows and columns on a chromium coated-substrate.

A robotic applicator with multiple capillary needles can be used. A single needle applicator using a pin which is washed between applications of different nucleic acids, or using a robotic pin changer also can be used. The needle used is preferably a 33 gauge, one-inch long stainless steel capillary syringe needle. The needle is connected to a nucleic acid reservoir, preferably a Luer lock syringe tip. a preferred needle and reservoir is available commercially from EFD, (East Providence, R.I.). It is preferred to use multiple capillary needles, each depositing a different nucleic acid, thereby eliminating a washing step between depositions.

Any suitable amount of nucleic acid is deposited in each target element, with the target element size dependent on the amount deposited. For each target element, the amount can be from about 0.05 nl to about 5.0 nl of a nucleic acid solution of 1 $\mu g/\mu l$ nucleic acid concentration. For a density of 1,000 target elements/$cm^2$, the individual amount deposited per target element is about 0.2 nl to about 2.0 nl of 1 $\mu g/\mu l$ solution. The nucleic acid is provided in any solvent that will permit deposition of denatured nucleic acid. Preferably, the nucleic acid is provided in 100 mM NaOH at 1 $\mu g/\mu l$ concentration.

To assist robotic manufacturing, automated tracking and labeling methods and apparatus can be used, for example, in delivering the correct nucleic acid for deposition at a particular target element. For example, bar coding or transponder labeling or tracking of capillary pins containing different nucleic acids are useful to assure delivery of the correct nucleic acid to the desired target element. The use of bar coding or transponder labeling also permits better computer control of the manufacturing process.

A microarray comprising both cDNA and genomic DNA target elements can be produced in any arrangement. For example, the cDNA elements can be located in one portion of the array or can be interspersed among the genomic DNA target elements. Although the regularity of a two dimensional array on a planar substrate surface is preferred to permit easy fluorescence detection and analysis, the array can be manufactured in any desired configuration.

Individual target elements can appear only once or can be replicated to provide statistical power to analysis of results. For arrays with densities under 3,000 target elements per $cm^2$, it is preferred to manufacture the array so that each target element is replicated three times on the array, to provide better calibration of the results. Applicants have determined that when using a microarray of less than one $cm^2$ of substrate surface area, the replicates can be placed adjacent each other or separated without material effect on the results.

Preferably, individual microarrays are manufactured on a large, substrate plate or wafer, which is scored using procedures well known in the semiconductor industry for breakup into individual chips. Chromium-coated glass plates or wafers are available commercially from Nanofilm (Westlake Village, Calif.) and can be scored using conventional procedures. Thus, multiple chips can be manufactured at once on the same wafer with one robotic applicator, and then separated into individual chips. Before printing, the wafers are preferably washed using, in order, distilled water, isopropanol, methanol and distilled water washes. Nitrogen is used to blow-off excess water and the rinsed wafers are dried.

The preferred Muller, et al. apparatus uses X-Y and Z axis controllers for the capillary pin applicator with application of a burst of low air pressure to deposit each nucleic acid. It is further preferred to use a suitable Z-axis controller on the apparatus of Muller, et al. to avoid contact of the capillary pin with the substrate surface. Positioning the pin above the surface, preferably about 100 μm above, permits better spot size regularity and use of lower air pressure.

When beginning printing, the plate or wafer is equilibrated to room temperature. The Z-axis height of each chip is then determined for use by the robot controller. Preferably, the printing starts with deposition of a 300 μdiameter "marker" spot in one corner of each chip for alignment control. The nitrogen pressure is low, preferably about 1 psi or less, and is a pressure sufficient to deposit the particular nucleic acid given its viscosity and amount to be deposited. The nitrogen pulse length is generally about 10 milliseconds.

It is also preferred to include various control target elements such as, for example, target elements comprising: (1) total genomic DNA, (2) vector DNA, (3) a pooled mixture of genomic DNA or cDNA from each target element, (4) total RNA from a normal tissue, or (5) total genomic or cDNA from a tissue with known abnormalities. The control target elements can also include a series of target elements each comprising a nucleic acid of known copy number for a particular expressed gene or genomic sequence. For example, genomic DNA extracted from cell lines with 1, 2, 3, 4 and 5 copies of the human X chromosomes can be used.

For quality control of the preferred robotic deposition manufacturing, it is preferred to image the produced arrays using a stereo microscope and a CCD camera. An image of each chip is captured and analyzed. Chips with missing, mis-sized or misshaped target elements are identified and marked.

When using cloned cDNA or cloned genomic DNA, the vector sequences can be removed before deposition with any suitable process or retained if they do not significantly interfere with the hybridization. For cloned genomic DNA and cDNA, it is preferred to not remove the vector sequences.

Any suitable substrate can be used, including those disclosed in U.S. Pat. Nos. 5,445,934 and 5,807,552. The substrate can be for example, without limitation, glass, plastics such as polystyrene, polyethylene, polycarbonate, polysulfone and polyester, metals such as chromium and copper, metal coated substrates and filters of any material. The substrate surface bearing the immobilized nucleic acids is preferably planar, but any desired surface can be used including, for example, a substrate having ridges or grooves to separate the array target elements. The nucleic acids can also be attached to beads, which are separately identifiable. The planar chromium-coated glass substrate of Muller, et al. is preferred.

The nucleic acids of the target elements can be attached to the substrate in any suitable manner that makes them available for hybridization, including covalent or non-covalent binding. The non-covalent attachment method of Muller, et al. is preferred.

(6) Tissue Nucleic Acids

The nucleic acid populations can be derived from any tissue source, including human, plant and animal tissue. The tissue sample comprises any tissue, including a newly obtained sample, a frozen sample, a biopsy sample, a blood sample, an anmiocentesis sample, preserved tissue such as a paraffin-embedded fixed tissue sample (i.e., a tissue block), or a cell culture. Thus, the tissue sample can comprise a whole blood sample, a skin sample, epithelial cells, soft tissue cells, fetal cells, amniocytes, lymphocytes, granulocytes, suspected tumor cells, organ tissue, blastomeres and polar bodies. The tissue to be tested can be derived from a micro-dissection process to produce a more homogeneous cell population. Paraffin fixed tissue is pretreated with any suitable process to remove the wax, and a paraffin pretreatment kit is available commercially from Vysis, Inc. Any suitable amount of tissue can be used, including a single cell, such as a human blastomere cell to be tested during in vitro fertilization procedures. Where only one or a few cells are available, such as when testing human fetal cells separated from maternal blood samples, a nucleic acid amplification technique to amplify the amount of nucleic acid can be used.

The nucleic acid populations derived from the tissue are produced by any suitable nucleic acid separation or purification process. Nucleic acid separation methods for both genomic DNA and for messenger RNA are available commercially, such as the QlAamp tissue kit for DNA isolation from Qiagen. For example, mRNA can be extracted from the tissue and then converted to cDNA by treatment with reverse transcriptase. If insufficient cDNA is available, the cDNA can be amplified by polymerase chain reaction. This well known process is called RT/PCR. It is also possible to convert the cDNA into a complementary RNA ("cRNA").

In general, where greater than about one million cells of tissue are available, the tissue nucleic acids can be extracted and used without amplification. If less than about one million cells are available, a nucleic acid amplification or concentration is preferably used. Preferably, such an amplification technique is PCR. Care and appropriate controls should be used with PCR to avoid or identify any artefacts introduced.

(7) Reference Nucleic Acids

The reference nucleic acid population is any suitable nucleic acid collection chosen to serve as a reference. For example, the reference population can be total human genomic DNA from normal tissue, total mRNA extracted from a normal sample of the tissue to be tested and converted to cDNA, or a synthetic or naturally-occurring mixture of cDNA for particular expressed genes. The reference can be a cRNA population. The reference also can include a "spiked," known amount of a particular genomic or cDNA sequence to enable control analysis.

(8) Labeling

The labels used can be any suitable non-radioactive marker detectable by any detection method. For example, the labels can be fluorescent molecules or can be proteins, haptens or enzymes. Also, "mass spec" labels, such as different isotopes of tin, can readily be detected after hybridization to the array by laser removal and mass spectrometry process, such as MALDI (matrix-assisted laser desorption-ionization). See Wu, et al., *Analytical Chemistry* 66, 1637 (1994) and Wu, et al., *Rapid Communications in Mass Spectrometry*, 7, 142 (1993). Preferably the labels are each fluorescent markers having sufficient spectral separation to be readily distinguished from each other without need of extensive "cross-talk" correction, such as fluorescein, Texas Red and 5-(and 6-)carboxytetramethyl rhodamine. An extensive list of fluorescent label compounds useful for attachment to nucleic acids appears in U.S. Pat. No. 5,491,224, "Direct Label Transaminated DNA Probe Compositions for Chromosome Identification and Methods for their Manufacture," Bittner, et al. Fluorescent compounds suitable for use are available commercially from Molecular Probe (Eugene, Oregon). Indirect labels, such as biotin and phycoerythrin, that are fluorescently labeled after hybridization to the array by contact with a fluorescent protein, such as avidin labeled with fluorescein, also can be used.

The reference population(s) and the tissue nucleic acid populations are labeled in any suitable manner, such as by end labeling, nick translation or chemical transformation. Preferably, during either the RT or PCR processing, a label incorporation step is used to label the resulting cDNA in a desired fluorescent color. The separated chromosomal DNA can be labeled using any suitable labeling chemistry, including end-labeling, nick translation and chemical labeling. It is preferred to use nick translation to label the chromosomal DNA in a suitable fluorescent color using a fluorescent dUTP or dCTP. Manufacture of suitable fluorescently labeled dCTP is disclosed in K. Cruickshank, Anal. Biochemistry, "Quantitation of Fluorescent Nucleotide Incorporation by Capillary Gel Electrophoresis and Laser Induced Fluorescent Detection," (in press), hereinafter referred to as "Cruickshank." Suitable nick translation kits are available commercially.

Preferably, for use of total human genomic DNA as the reference population, the labeling is done by a bisulfite-catalyzed transamination process as disclosed in U.S. Pat. No. 5,506,350, "Production of Chromosome Region Specific DNA Sequences and Transamination," Bittner, et al. Total human genomic DNA labeled by such a process is available commercially from Vysis, Inc. (Downers Grove, Ill.).

The labeling method used preferably results in a label content of each nucleic acid population of about 0.3 to about 6.0 mole percent labeled nucleotides when using direct attachment of fluorophores to the nucleic acids. The quantities of each labeled tissue nucleic acid and reference nucleic acid to be used are preferably in the range of about 100 ng to about 1 $\mu$g, preferably about 300 ng to about 425 ng.

(9) Array Hybridization

The tissue and reference nucleic acid populations are hybridized to the array under suitable hybridization conditions, i.e., stringency, for a time selected to permit detection of hybridization of single copy genomic sequences. The hybridization conditions include choice of buffer, denaturant, such as formamide, salt additives and accelerant. Hybridization buffers containing formamide and dextran sulfate at specified pH and salt conditions, such as LSI Hybridization Buffer (Vysis, Inc.), are available commercially. The buffer will preferably have a pH of about 6.8 to about 7.2, a salt content of about 1.5×SSC to about 2.5×SSC, and a formamide content of about 40–50%. Suitable conditions can include a temperature of about 40 to about 80 degrees centigrade for a time sufficient to detect signal over background for both genomic and expression of about 1 to about 72 hours, preferably 12–24 hours. Hybridization accelerators, such as dextran sulfate, can be used if desired. Adequate diffusion of the tissue and nucleic acid populations into contact with all target elements is necessary. This can be achieved by simple diffusion, or by accelerating diffusion or overcoming diffusion limitations using any suitable means including mechanical mixing, such as by rocking, or fluidic diffusion, such as by microfluidic pumping of the labeled populations in and out of a hybridization chamber containing the array. The post-hybridization wash is preferably at a stringency greater than that of the hybridization.

When using an array comprising human genomic DNA target elements, it is also preferable to add to the hybridization mix an excess of unlabeled human repeat sequence DNA, such as Cot1 DNA available from Life Technologies, Inc., to suppress the non-specific signal resulting from hybridization of labeled repeat sequences present in the tissue nucleic acid population or in a reference genomic DNA, if used. Use of unlabeled repeat sequence DNA is generally in amounts of about 0.02 to about 5.0 $\mu$g per 1 ng of total labeled genomic DNA (both tissue and reference), and preferably about 0.1 to 0.5 $\mu$g per 1 ng total labeled genomic DNA.

Figure 2A:
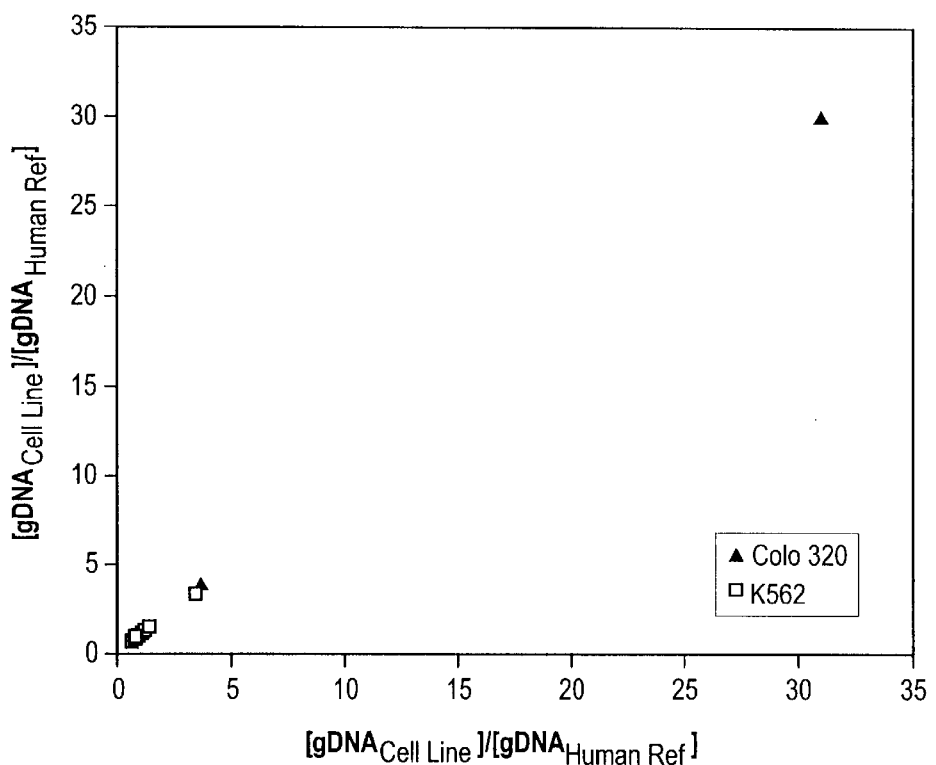
FIGS. 2(*a*) through 2(*h*) depict data from a nucleic acid microarray after hybridization with tissue cDNA and genomic DNA populations, each derived from a human cancer cell line, one labeled red, the other green, and a total human genomic DNA reference population labeled orange, which show the capability of the method of the invention to detect simultaneously both gene expression and chromosomal abnormalities on the same nucleic acid microarray.

The hybridization can be performed in any suitable apparatus that will maintain the populations in contact with the array for a suitable time. For example, the labeled populations can be added to the array, covered with a cover slip and then incubated in an oven at the preselected temperature. Preferably, a cover slip designed to provide a desired hybridization volume between its bottom surface and the top of the array substrate is used. The labeled populations can be added to an array contained in a sealed cartridge apparatus, such as disclosed in European Patent Application 0 695 941 A1, "Method and Apparatus for Packaging a Chip," published Feb. 7, 1996, by microfluidic injection and circulation. The hybridization also can be carried out in a miniaturized hybridization and assay chip, such as that disclosed in PCT Patent Application WO 97/02357, "Integrated Nucleic Acid Diagnostic Device," published Jan. 23, 1997. Such miniaturized chips are referred to as manufactured on a mesoscale, i.e., manufactured having volumes for fluid pathways and reaction chambers measured in amounts of $10^{-8}$ and $10^{-9}$ liters. FIGS. 2(a) through 2(e) show components of a preferred hybridization cartridge. FIG. 2(a) displays the first component, a chromium coated glass "chip" 30 containing the immobilized nucleic acid target elements 31 of the microarray 32. The microarray 32 is preferably located in the center of the chip 30, as shown. In a preferred format, the chip is 25.4 mm long×16.93 mm wide×0.7 mm thick; and the microarray covers a 10.5 mm long×6 mm wide area. Shown in FIG. 2(b), the second component is a "probe clip" 33, depicted with two alternate shapes, square and circular, for "array window" 34. The probe clip 33 can be made from any suitable material, preferably plastic. The array window 34 is of a clear material, and is located and sized to permit ready imaging of the microarray. The probe clip 33 forms a hybridization chamber and fits snuggly over the array as a retainer and protective cover. Preferably, the array window 34 is 1.27 mm in diameter, centrally located in a 25.4 mm long×16.76 mm wide probe clip 33.

Figure 2B:
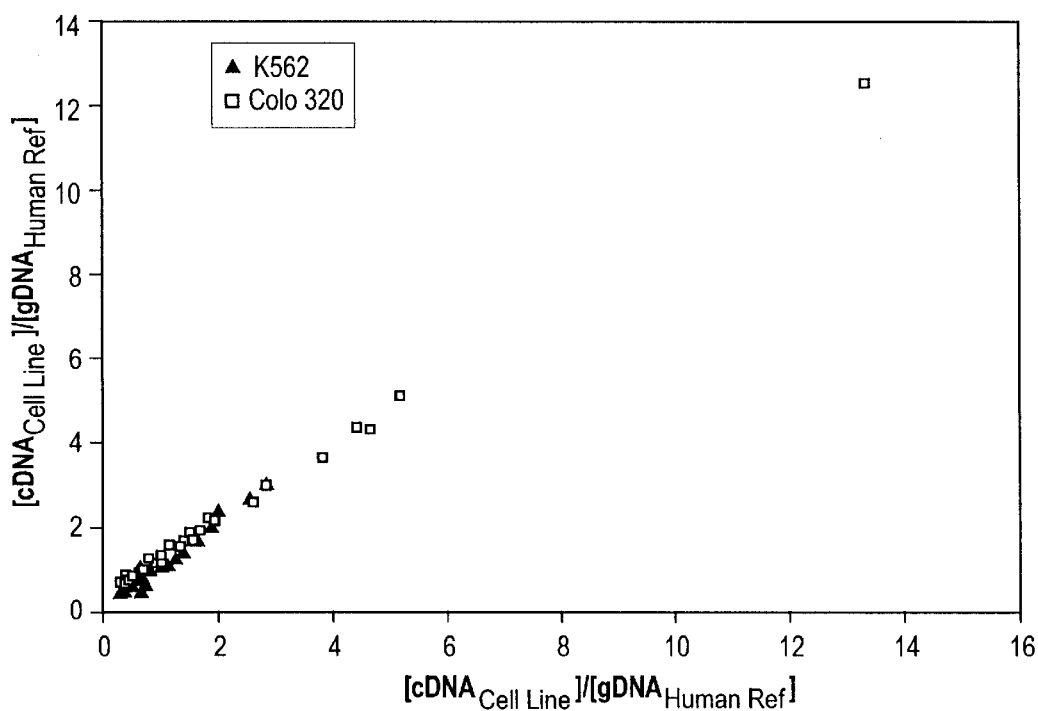
Figure 2C:
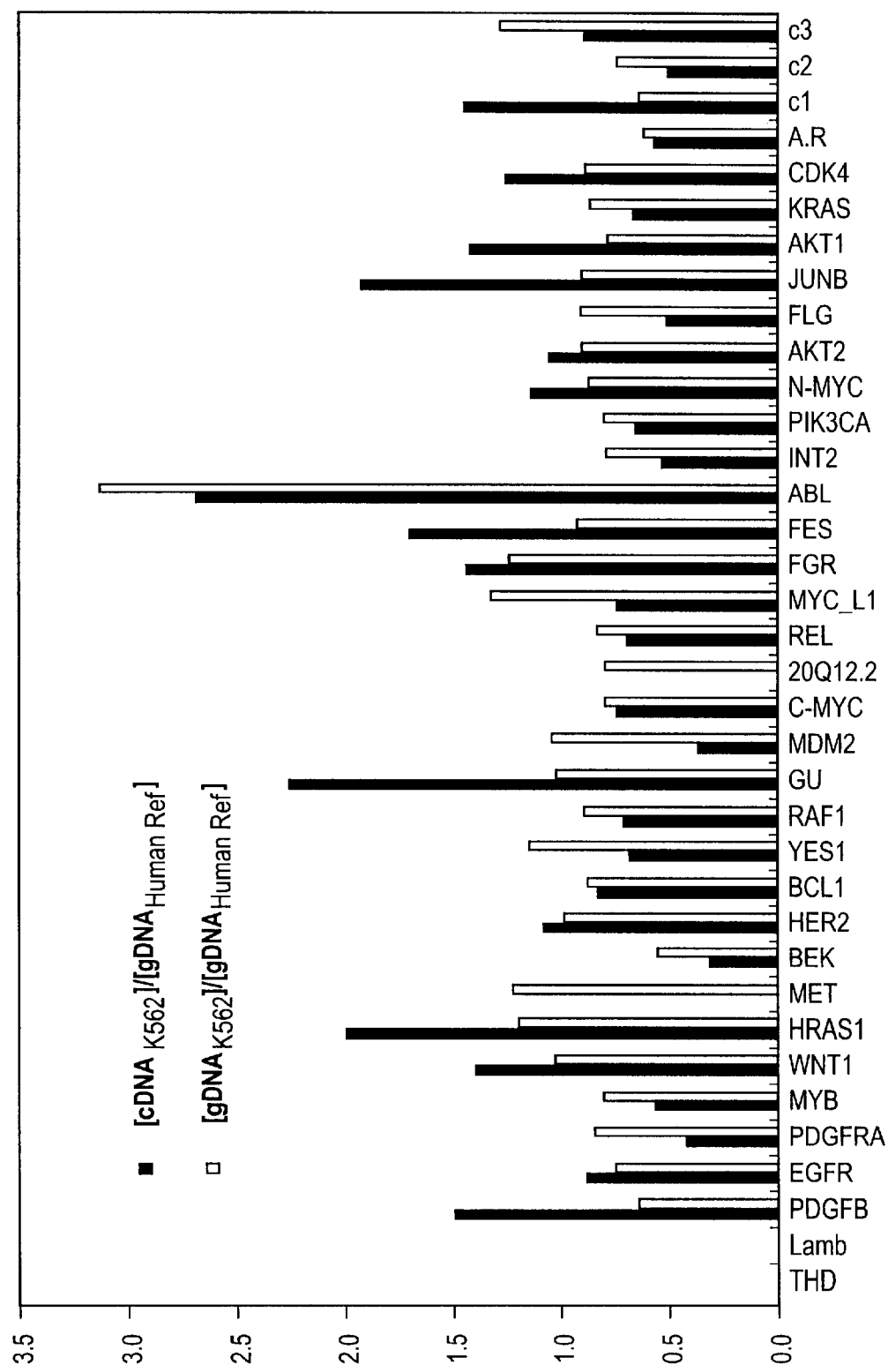
Figure 2D:
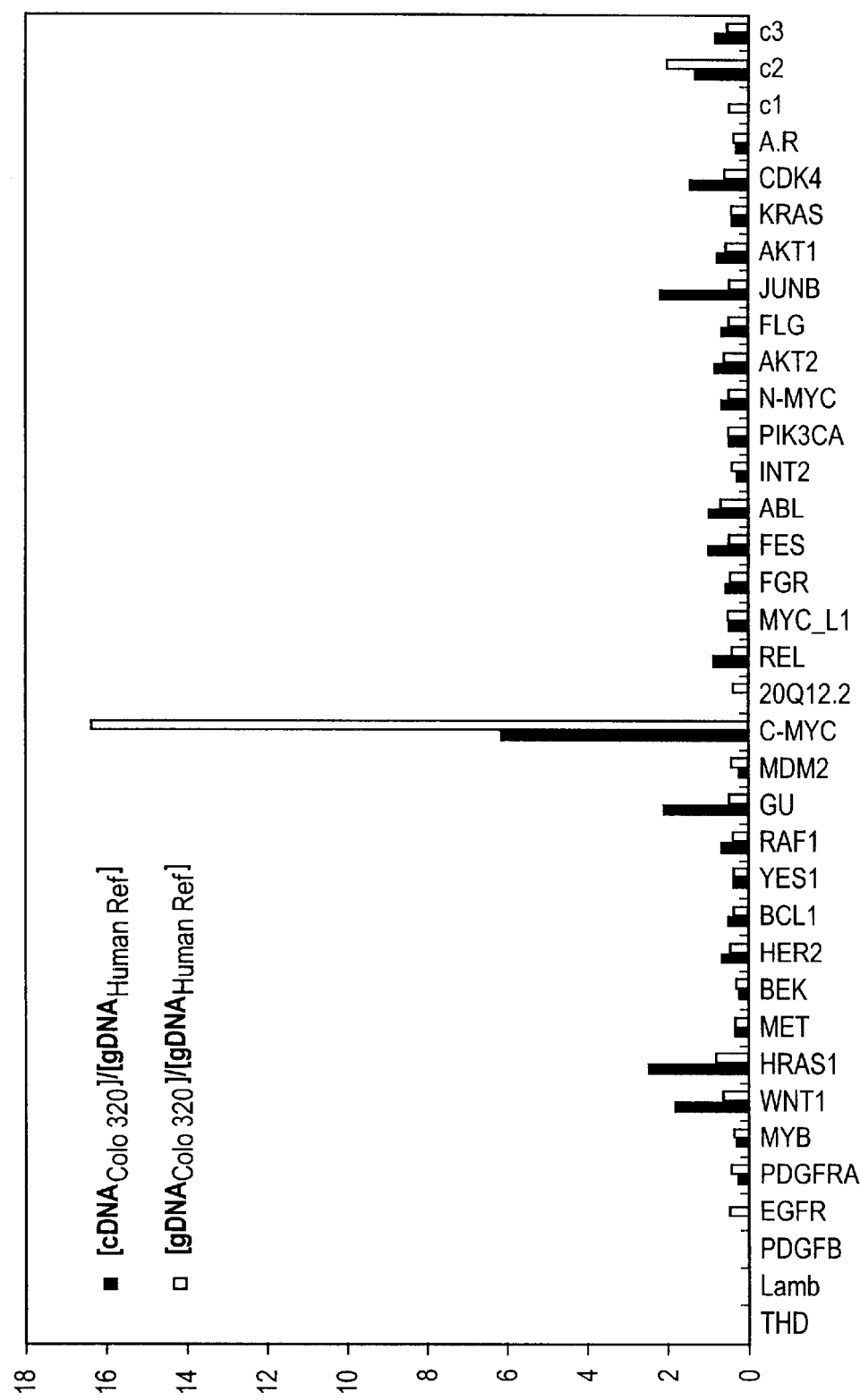

FIGS. 2(c) and 2(d) are top and side views of the fourth component, a chip holder 36, preferably made of a sturdy, injection moldable plastic, such as high-impact polystyrene, which is capable of withstanding necessary hybridization temperatures without loss of physical stability. The chip holder 36 can be of any desirable dimension for holding the chip, and preferably is 25.4 mm wide×76.2 mm long×3.2 mm thick. As shown, near one end, the chip holder 36 contains a cavity 37, preferably 26 mm long×18.5 mm wide×17 mm deep, sized to accept the chip 30 bearing the microarray 32. The cavity 37 along its length is also slightly wider, preferably 0.5mm on each side, to create an access gap 38 to permit easier addition and removal of the probe clip and microscope cover slip. The surface of the cavity bottom is scored with shallow grooves to facilitate spreading of adhesive or fixative designed to hold the chip in place. The chip holder 36 at the end opposite the cavity 37 can be lightly scored across the width of the holder on its upper surface to provide a more grippable surface for the user. The chip holder bottom can be grooved to facilitate alignment in an array reader.

Figure 2E:
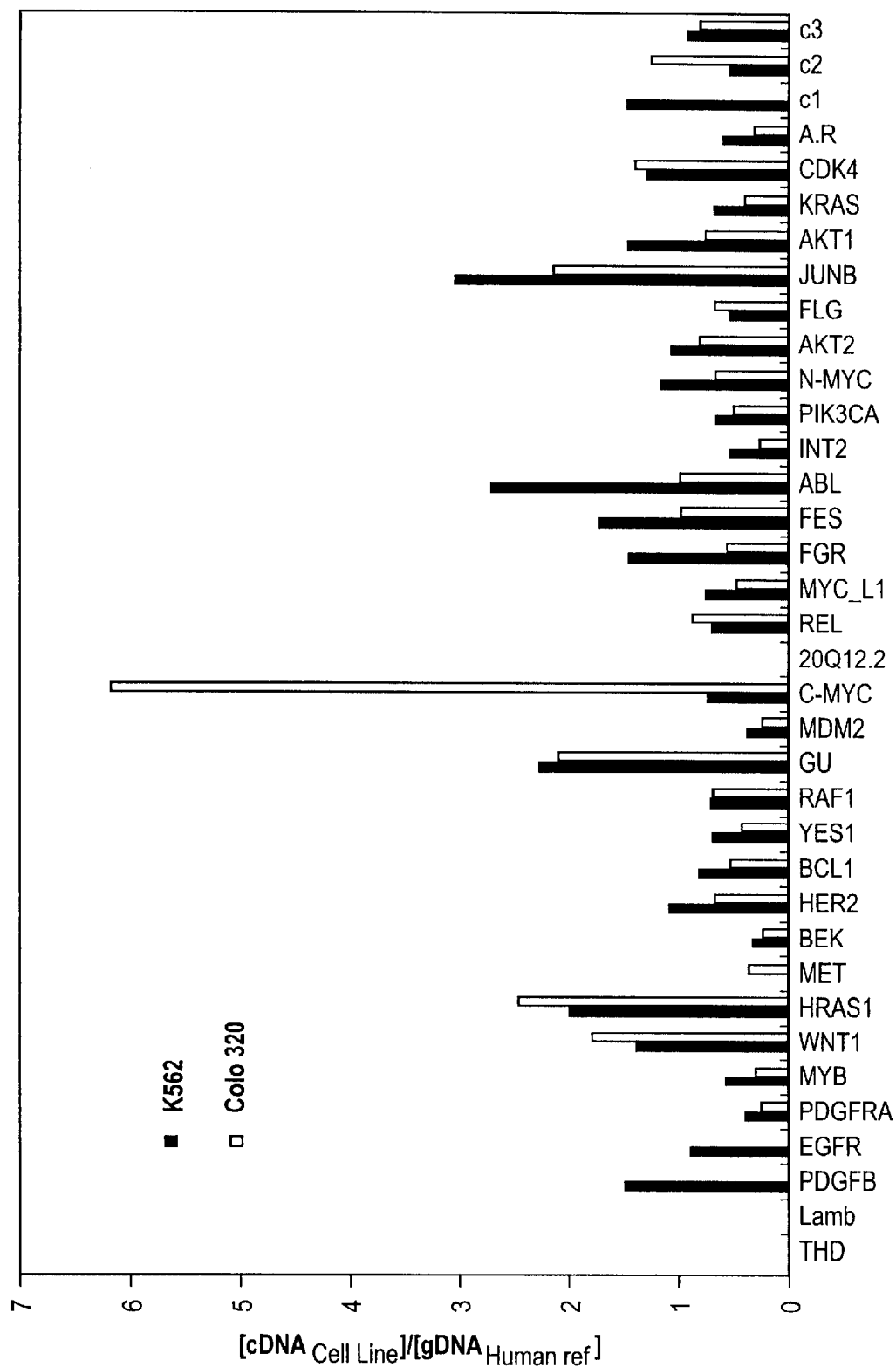

In manufacture of the completed cartridge, a microarray with desired target elements is manufactured as described above, and is then glued with any suitable adhesive into the bottom of cavity 37. The chip holder 36 bearing the array can then be shrink wrapped, and enclosed in a kit with the probe clip 33, a cover slip used in array imaging, and any other desirable reagents for labeling or extracting nucleic acids and/or performing the hybridization. To carry out the method of the invention, the user applies the hybridization solution comprising an appropriate buffer and the labeled nucleic acid populations (reference and tissue) to the surface of the microarray, and places the probe clip 33 on top of the microarray. The completed cartridge is depicted in FIG. 2(e). Also shown superimposed in FIG. 2(e) is the camera field of view 35 for the preferred imaging system of Che. The cartridge is then incubated in an oven, with desired humidity control at the desired hybridization temperature for the desired time.

When the hybridization is completed, the probe clip 33 is removed and the chip washed at a desired stringency, preferably, in order with 2×SSC at room temperature for 5 minutes, with 2×SSC and 50% formamide at 40° C. for 30 minutes, and 2×SSC at room temperature for 10 minutes, to remove hybridized probe. Gel/Mount (Biomeda, Foster City, Calif.) and DAPI is applied to the array and a 18 mm×18 mm glass microscope cover slip is sealed over the array, still in holder 36. The covered chip is then imaged to detect the hybridization results.

(10) Array Detection

After hybridization, the fluorescence presence and intensity for each label color is detected and determined by any suitable detector or reader apparatus and method. Laser-based array scanning detectors are known to the art, see U.S. Pat. No. 5,578,832, "Method and Apparatus for Imaging a Sample on a Device," Trulsen, et al. Optical waveguide detection methods for array hybridization also have been disclosed, see U.S. Pat. No. 5,843,651, "Light Scattering Optical Waveguide Method for Detecting Specific Binding Events," D. Stimpson, et al. Preferably, a large field imaging apparatus and method, such as disclosed in co-pending, commonly assigned U.S. patent application Ser. No. 09/049,798, "Large-Field Fluorescent Imaging Device," filed Mar. 27, 1998, U.S. Pat. No. 5,947,303, D. Che, (herein referred to as "Che") is used.

The large-field fluorescence imaging apparatus of Che uses reflective optics to couple the excitation beam generated by a high-power white light source onto the microarray surface to provide a high illumination intensity, and combines the high illumination intensity with the high detection efficiency of an array detector to provide a high image acquisition rate. The white light generated by the light source is collimated and filtered with a computer-controlled filter to provide the excitation beam. The excitation beam is passed through a field stop to form a well-defined beam pattern and then projected onto the array surface with a concave mirror. The concave mirror is disposed to image the field stop on the sample to define an illumination area which matches the field of view of the imaging optics. The fluorescent light generated in the sample is color filtered to reject scattered light of excitation color and imaged by the imaging optics onto the array detector to produce a fluorescent image of the sample.

The array imaging apparatus and method may employ digital image processing algorithms used in a programmed computer for data analysis, storage and display of digital image data from the imaging apparatus. Any suitable digital image processing, data storage and display software can be used for analysis of the array hybridization results. Digital imaging methods are known to those skilled in the art, for example, as disclosed in U.S. Pat. No. 5,665,549, "Comparative Genomic Hybridization," Kallionemi, et al., and U.S. Pat. No. 5,830,645.

The hybridization images are preferably captured and analyzed by use of a high resolution digital imaging camera, such as a SenSys 1600 Camera with PSI interface from Photometrics (Scottsdale, Ariz.), which receives the large field image directly from the detection optics. Any other suitable camera can also be used. The raw image data captured by the camera is stored in any suitable computer data base or data storage file. The raw image data is processed using suitable image analysis algorithms to determine the marker intensity at each target element of the microarray. Image analysis algorithms are well known to those skilled in the art, and a package of a large number of such algorithms is available as IPLab from Scanalytics (Fairfax, Va.)

Preferably, the image analysis algorithms carry out the following operations, implemented in appropriate computer software: (i) background correction, as necessary; (ii) array target element or "spot" segmentation for identification of individual array elements; (iii) spot grid assignment of a column and row number to each spot; (iv) spot data analysis, including verification of validity and presence of artifacts, averaging of data for replicate spots, normalization of data from all spots, and multi-experiment comparison and analysis; (v) single spot calculations, including the total intensity of each fluorescent marker color, the average DAPI counterstain intensity, the mean, mode, median and correlation coefficient of the per pixel ratios of fluorescent intensities, and the ratio of total tissue nucleic acid marker intensity to reference intensity, termed as the "mass ratio"; (vi) target summary analysis, including the number of valid replicates for a spot, the mean and coefficient of variation of the per spot mass ratios and the correlation coefficient of per pixel ratios across all spots. Preferably, the image analysis used standardizes the mean mass ratio such that the modal value is 1.00 using a window-based estimate of the mode.

The fluorescent data at each target element can be compared automatically to produce the ratio between any desired tissue and reference or between tissues. For example, when using four tissue nucleic acids (primary tumor genomic DNA and cDNA and metastasis genomic DNA and cDNA) with two references (total genomic and total cDNA from normal tissue of the same cell type as the tumor), at least eight different ratios can be calculated (the ratio of each reference with each tissue).

The image analysis also preferably comprises implementation of criteria set by the individual user for valid analyses, including (vii) exclusion of spots with pixels having saturated tissue or reference color channels; (viii) spot size and shape criteria for exclusion; and (ix) a "relation coefficient" exclusion for spots with relative coefficient values below threshold. The array data analysis can also include comparison algorithms to compare data from individual tests to data bases containing disease genotypes and phenotypes (i.e. listing of gene expression and chromosome abnormalities for particular diseases), which can identify possible diagnosis or choice of therapy based upon individual test results.

The image analysis preferably uses computer display and printing algorithms, such as those, for example, known to one of skill in the art, for computer monitor display and computer printing. The data display can include "pseudo-color" images selected by the user for the individual fluorescent colors of the tissue and reference nucleic acids. The array data display can be coupled with display of conventional chromosome ideograms to more clearly detail chromosome abnormalities and expressed gene abnormalities identified by the method of the invention. See U.S. Pat. No. 5,665,549, FIG. 9, for an exemplary ideogram. Preferably, the array data is also displayed so that spots excluded from analysis are marked for ready identification by the user. This can be done by displaying that target element in an "error color" or with a colored circle around it.

In the preferred embodiment, the array reader and software automatically capture four images of each chip, specific for: (1) the DAPI counterstain (blue), (2) the tissue DNA (green), (3) the tissue cDNA (red), and (4) the reference DNA (orange). These images are referred to as color planes. However, images for more or different color planes can be taken. The image analysis portion of the software preferably uses one of the colors (preferably the DAPI image) to identify target elements and their location in the grid. Once all spots are identified the software analyses each pixel under each spot for its intensity in each of the remaining color planes. Suitable algorithms are employed to determine the local background for each of these color planes, which is then subtracted from the total intensity of each color. The background corrected intensities can then be averaged for all pixels under a particular target spot or group of spots, and this average intensity per pixel (e.g., A for DAPI intensity, B for tissue DNA intensity, C for tissue cDNA intensity and D for reference intensity) can be used for various analyses.

For example, the intensity A may be used as an indicator of target spot quality, since the intensity of DAPI staining is a function of total amount of DNA attached at the target spot. Below a certain value for A (under controlled staining conditions) the amount of target element DNA may become rate limiting. The intensity D of the reference DNA can be used as an indicator for the efficiency of hybridization, since this reagent is preferably provided in a pre-determined concentration and is quality controlled.

In the preferred analysis, the most important information is the ratio of background corrected tissue intensity over background corrected reference intensity; i.e. for the above example the ratios of B/D and C/D. If more than one reference is used, then additional ratios can be taken to give informative data. These ratios can be determined for a group of spots, a single spot, or for each pixel under each spot.

In the most preferred mode, and for the example listed above, the B/D and C/D intensity ratios are being determined for each pixel, which should be independent on their absolute intensity in any of the colors. In other words, a plot of B versus D, for example, for each pixel under each spot should yield a scatter around a straight line, which should intersect both the X and Y axis at O, if the background correction was appropriate. (Appropriate algorithms can generate such a plot by "clicking" on a given target spot or group of spots in the display.) This plot reveals two types of information:

First, the amount of scatter around the linear regression line is indicative of the quality of the data, and can be statistically evaluated to generate a correlation coefficient, which for ideal spots is 1 (i.e. all pixel values fall on the regression line). A value less than 1 indicates less than perfect data, and a value of 0.8 or less is preferably taken as an indicator that data from such a spot should be considered suspect. This scatter plot can be generated for a single spot or group of spots. Second, the slope of this regression line is the B/D or C/D intensity ratio, respectively, for a given spot or group of spots.

In order to extract the desired biological information, the B/D or C/D ratio is preferably normalized with respect to a control spot or group of spots, for which these ratios can be correlated to a known level of DNA or RNA sequence in the test probe mixture. This is done as follows:

For analysis of genomic DNA the assumption is made that most of the tissue DNA sequences are in fact present in their normal copy number, i.e. two per genome (except for sequences from the sex chromosomes if the test tissue is from a male donor). For the reference DNA this is assumed to be true for all sequences (other than those from X or Y chromosomes if the reference DNA is from a male donor). Based on these assumptions the software compares the B/D or C/D ratios of all target spots and selects a group of ratios that appear to be very similar. This group of ratios is assumed to represent targets that are normal in the test tissue, and the average of that ratio is used to normalize all other ratios. In other words, the B/D or C/D ratios of all spots will be divided by the average B/D or C/D ratio, respectively, of this "normal group." Thus, the B/D or C/D ratios of all normal spots should be close to 1, while the B/D or C/D ratios from targets that are aneuploid (present in copy numbers larger or smaller than 2), will be around 0.5 or less (deletions) or 1.5 or above (additions or amplifications).

The inventive combination of simultaneous expression and genomic analysis allows a correlation of the expression level to the gene copy number, by using the ratios described above as follows:

Assume that an assay was performed in which B is the intensity for the tissue genomic DNA, C is the intensity for tissue mRNA (cDNA) and D is the intensity for the reference genomic DNA. Then, the ratios to be obtained are as follows:

(B/D)=background corrected average pixel intensity ratio
($B_g/D_g$)=background corrected average pixel intensity ratio average for "normal" subgroup
(B/D)/($B_g/D_g$)=normalized B/D ratio=$B_n/D_n$
(C/D)=background corrected average pixel intensity ratio
($C_g/D_g$)=background corrected average pixel intensity ratio average for "normal" subgroup
(C/D)/($C_g/D_g$)=normalized C/D ratio=$C_n/D_n$ The $B_n/D_n$ ratio reveals the number of genomic copies of a given target sequence, the $C_n/D_n$ ratio reveals the relative number of mRNA copies per genomic sequence, and the $C_n/B_n$ ratio would indicate whether the relative mRNA copy number correlates with a relative change in the genomic copy number change.

(11) Example Arrays

Exemplary of the types of microarrays useful in the method of the invention is a prenatal array of about 100 target elements without replicates, which comprise genomic DNA sequences from (a) the unique sequence regions immediately adjacent the repeat sequence regions of (i) all human telomeres and (ii) all human centromeres (taken from both p and q arm); (b) the "microdeletion" syndrome regions for DiGeorge, Smith-Magenis, Downs, Williams, Velocardiofacial, Alagille, Miller-Dieker, Wolf-Hirschhorn, Cri du Chat, Cat Eye, Langer-Giedion, Kallmann and Prader-Willi/Angelman syndromes; and (c) deletion regions identified with sterylsulfatase deficiency, muscular dystrophy and male infertility, and those believed tied to mental retardation that involve deletion of the sub-telomeric, unique sequence regions on each chromosome.

Table 1 lists human genomic DNA clones useful in such an array. This prenatal array has powerful medical utility because of its capability to reliably detect multiple gross chromosomal changes causing inherited disease. The human prenatal array is also useful for post-natal testing, for fetal cell testing and for pre-implantation genetic testing on blastomeres and polar bodies. Table 1 includes the chromosomal loci and the disease correlated to each loci.

TABLE 1

Prenatal Chip-Loci To Detect Copy Number Abnormalities in Non-Cancer Genetic Diseases

| Gene or Chrom. Locus | Cyto. Loc. | Disease |
|---|---|---|
| 1 p tel | 1 p tel | Mental Retardation, other |
| p 58 | 1 p 36 | 1 p 36 deletion syndrome |
| 1 near cen |  | aneusomy & region marker |
| 1 q tel | 1 q tel | Mental Retardation, other |
| 2 p tel | 2 p tel | Mental Retardation, other |
| 2 ner cen |  | aneusomy & region marker |
| 2 q tel | 2 q tel | Mental Retardation, other |
| 3 p tel | 3 p tel | Mental Retardation, other |
| 3 near cen |  | aneusomy & region marker |
| 3 q tel | 3 q tel | Mental Retardation, other |
| 4 p tel | 4 p tel | Mental Retardation, other |
| WHSCR/WHSC | 4 p 16.3 | Wolf-Hirschhorn syndrome |
| 4 near cen |  | aneusomy & region marker |
| 4 q tel | 4 q tel | Mental Retardation, other |
| D5S23 | 5 p 15.2 | Cri du chat syndrome |
| 5 p tel | 5 p tel | Mental Retardation, other |
| 5 near cen |  | aneusomy & region marker |
| 5 q tel | 5 q tel | Mental Retardation, other |
| 6 p tel | 6 p tel | Mental Retardation, other |
| 6 near cen |  | aneusomy & region marker |
| 6 q tel | 6 q tel | Mental Retardation, other |
| 7 p tel | 7 p tel | Mental Retardation, other |
| 7 near cen |  | aneusomy & region marker |
| 7 q tel | 7 q tel | Mental Retardation, other |
| Elastin | 7 q 11.23 | Williams syndrome |
| 8 p tel | 8 p tel | Mental Retardation, other |
| 8 near cen |  | aneusomy & region marker |
| 8 q tel | 8 q tel | Mental Retardation, other |
| EXT1 | 7 q 24.1 | Langer-Giedion syndrome |
| 9 p tel | 9 p tel | Mental Retardation, other |
| 9 near cen |  | aneusomy & region marker |
| 9 q tel | 9 q tel | Mental Retardation, other |
| 10 p tel | 10 p tel | Mental Retardation, other |
| 10 near cen |  | aneusomy & region marker |
| 10 q tel | 10 q tel | Mental Retardation, other |
| WI-8545 | 10 p 14–p 13 | Velocardiofacial/DiGeorge syndromes |
| 11 p tel | 11 p tel | Mental Retardation, other |
| 11 near con |  | aneusomy & region marker |
| 11 q tel | 11 q tel | Mental Retardation, other |
| 12 p tel | 12 p tel | Mental Retardation, other |
| 12 near cen |  | aneusomy & region marker |
| 12 q tel | 12 q tel | Mental Retardation, other |
| 13 near cen |  | chromosome poidy & region marker |
| 13 q tel | 13 q tel | Mental Retardation, other |
| RB1 | 13 q 14 | Trisomy 13, other |
| 14 q tel | 14 q tel | Mental Retardation, other |
| 14 near cen |  | chromosome poidy & region marker |
| 15 q tel | 15 q tel | Mental Retardation, other |
| 15 near cen |  |  |
| SNRPN | 15 q 11–q 13 | Prader-Willi/Angelman syndromes |
| D15S10 | 15 q 11–q 13 | Prader-Willi/Angelman syndromes |
| 16 p tel | 16 p tel | Mental Retardation, other |
| 16 near cen |  | aneusomy & region marker |
| 16 q tel | 16 q tel | Mental Retardation, other |
| 17 p tel | 17 p tel | Mental Retardation, other |
| FLII | 17 p 11 | Smith-Magenis syndrome |
| PMP22 or adjac | 17 p 12 | CMT1A/HNNPP |
| D17S258 | 17 p 13 | Miller-Dieker syndrome/Isolated Lissencephally |
| LIS1 | 17 p 13 | Miller-Dieker syndrome/Isolated Lissencephally |
| 17 near cen | 17 p 13 | aneusomy & region marker |
| 17 q tel | 17 q tel | Mental Retardation, other |
| 18 near cen |  | aneusomy & region marker |
| 18 p tel | 18 p tel | Mental Retardation, other |
| 18 q tel | 18 q tel | Mental Retardation, other |
| 18 p 11.3 probe | 18 q 11.3 | Tri/Iso Chromosome 18 p |
| 19 p tel | 19 p tel | Mental Retardation, other |
| 19 near cen |  | aneusomy & region marker |
| 19 q tel | 19 q tel | Mental Retardation, other |
| 20 p tel | 20 p tel | Mental Retardation, other |
| JAG1 | 20 p 11 | Alagille syndrome |
| 20 near cen |  | aneusomy & region marker |
| 20 q tel | 20 q tel | Mental Retardation, other |
| 21 q tel | 21 q tel | Mental Retardation, other |
| 21 near cen |  | aneusomy & region marker |

TABLE 1-continued

Prenatal Chip-Loci To Detect Copy Number Abnormalities in Non-Cancer Genetic Diseases

| Gene or Chrom. Locus | Cyto. Loc. | Disease |
|---|---|---|
| MNB or D21S55 | 21 q 22.1 | Down syndrome |
| ERG | 21 q 22.1 | Down syndrome |
| 22 q tel | 22 q tel | Mental Retardation, other |
| 22 q near cen | | Cat Eye syndrome |
| GSCL | 22 q 11 | Velocardiofacial/DiGeorge syndromes |
| HIRA, TUPLE 1 | 22 q 11 | Velocardiofacial/DiGeorge syndromes |
| X/Y p tel | X/Y p tel | Mental Retardation, other |
| STS | Xp 22.3 | Ichthyosis, x-linked |
| KAL | XP 22.3 | Kallmann syndrome |
| AR | Xq 11–q 12 | aneusomy & region marker |
| XIST | Xq 13.2 | Region marker |
| Dystrophin exon | Xp 21 | Muscular Dystrophy |
| X/Y q tel | X/Y q tel | Mental Retardation, other |
| SRY | Yp 11.3 | xx males, etc. |
| AZFB | Yq 11.2 | male infertility/Yq marker |
| AZFC | Yq 12 | male infertility/Yq marker |

Another example is the AmpliOnc™ genomic DNA target element array containing genomic sequences for each of the 52 oncogene or amplified gene loci listed in Table 2.

TABLE 2

AmpliOnc Loci

| Gene or Chrom. Locus | Cyto. Location | Cancer Association |
|---|---|---|
| NRAS | 1 p 13.2 | Breast cell line |
| MYCL1 | 1 p 34.3 | Small cell lung cancer cell line, neuroblastoma cell line |
| FGR | 1 p 36.2–p 36.1 | |
| LAMC2 | 1 q 25–q 31 | Breast cell line |
| REL | 2 p 13–p 12 | Non-Hodgkin's Lymphoma |
| ALK | 2 p 23 | lymphoma |
| MYCN (N-myc) | 2 p 24.3–q 24.1 | Neuroblastoma |
| RAF1 | 3 p 25 | Non-small cell lung cancer |
| TERC (hTR) | 3 q 26 | Cervical, Head & Neck, Lung |
| PIK3CA | 3 q 26.3 | Ovarian |
| BCL6 | 3 q 27 | lymphoma |
| PDGFRA | 4 q 11–q 12 | Giloblastoma |
| MYB | 6 q 22 | Colorectal; Leukemia; Melanoma |
| ESR1 (ER, ESR) | 6 q 25.1 | Breast |
| EGFR (ERBB1, ERBB) | 7 p 12.3–p 12.1 | Glioma; Head & Neck |
| PGY1, MDR1 | 7 q 21 | Drug resistant cell lines |
| MET | 7 q 31 | Gastric |
| FGFR1, FLG | 8 p 11.2–p 11.1 | Breast |
| MOS | 8 q 11 | Breast |
| ETO, MTG8, CBFA2T1 | 8 q 22 | leukemia |
| MYC (c-myc) | 8 q 24.12–q 24.13 | Small cell lung, Breast, Esophageal, Cervical, Ovarian, Head & Neck, etc. |
| ABL1 (ABL) | 9 q 34.1 | CML |
| FGFR2 (BEK) | 10 q 26 | Breast |
| HRAS | 11 p 15.5 | Colorectal, Bladder |
| CCND1 (Cyclin D1, BCL1) | 11 q 13 | Head & Neck, Esophageal, Breast, Hepatic, Ovarian |
| FGF4 (HSTF1, HST) | 11 q 13 | Breast, Ovarian |
| FGFF3 (INT2) | 11 q 13 | Breast, Ovarian, Gastric, Melanoma, Head & Neck |
| EMS1 | 11 q 13 | Breast, Bladder |
| GARP(D11S833E) | 11 q 13.5–q 14 | Breast |
| PAK1 | 11 q 13.5–q 14 | Breast |
| MLL (ALL1) | 11 q 23 | leukemia |
| KRAS2 | 12 p 12.1 | Colorectal, Gastric, Adenocortical, Lung giant cell |
| CCND2 (Cyclin D2) | 12 p 13 | Lymphoma, CLL |
| TEL (ETV6) | 12 p 13 | leukemia |
| WNT1 (INT1) | 12 q 12–q 13 | Retinoblastoma |
| SAS; CDK4 | 12 q 13–q 14 | Sarcoma, glioma |
| GL1 | 12 q 13.2–q 13.3 | Sarcoma, glioma |
| MDM2 | 12 q 14.3–q 15 | Sarcoma, glioma |

TABLE 2-continued

AmpliOnc Loci

| Gene or Chrom. Locus | Cyto. Location | Cancer Association |
|---|---|---|
| AKT1 | 14 q 32.3 | Gastric |
| PML | 15 q 22 | leukemia |
| IGF1R | 15 q 25–q 26 | rare amplicon |
| FES | 15 q 26.1 | rare amplicon |
| MRP | 16 p 13.1 | Drug resistant cell lines |
| MYH11 | 16 p 13.13–p 13.12 | leukemia |
| CBFB | 16 q 22 | leukemia |
| RARA | 17 q 12 | leukemia |
| HER-2/neu (EGFR2) | 17 q 12–21 | Breast, Ovarian, Gastric |
| TOP2A | 17 q 21–q 22 | |
| YES1 | 18 p 11.3 | Gastric |
| BCL2-3' segment | 18 q 21.3 | Non-Hodgkin's Lymphoma |
| BCL2-5' segment | 18 q 21.3 | Non-Hodgkin's Lymphoma |
| INSR (insulin receptor) | 19 p 13.2 | Breast |
| JUNB | 19 p 13.2 | HeLa cell lines |
| CCNE (Cyclin E) | 19 q 12 | Gastric, Ovarian |
| BCL3 | 19 q 13 | lymphoma |
| AIB1 | 20 q 12 | Breast |
| CSE1L (CAS) | 20 q 13 | Breast |
| MYBL2 | 20 q 13.1 | Breast |
| PTPN1 | 20 q 13.1–q 13.2 | Breast |
| ZNF217 (ZABC1) | 20 q 13.2 | Breast |
| STK15 (BTAK, aurora 2) | 20 q 13.2 | Breast, ovarian, colon, prostate, neuroblatoma and cervical |
| AML1 (CBFA2) | 21 q 22.3 | leukemia |
| BCR | 22 q 11.21 | leukemia |
| EWSR1 (EWS) | 22 q 12 | sarcoma |
| PDGFB (SIS) | 22 q 12.3–q 13.1 | Rhabdomyosarcoma, liposarcoma |
| AR | Xq 11.2-q 12 | Prostate |

Note: Alternate names for a gene are shown in parentheses.

Genomic DNA target elements derived from the clones listed in Table 2 contain human genomic DNA inserts of about 50 kb to about 200 kb in a PAC, P1 or BAC vector. This array is produced without separation of the vector sequences. Use of this array permits simultaneous identification of genomic amplification of each of these oncogene loci, as well as expression of the genes which map into these regions.

Yet another example is an AmpliOnc II array, which contains genomic DNA from the oncogene loci of Table 2, supplemented by genomic DNA from the human tumor suppressor gene loci for: the p53, RB1, WT1, APC, NF1, NF2, VHL, MEN1, MENZA, DPC4, MSH2, MCH1, PMS1, PMS2, P57/KIP2, PTCH, BRCA1, BRCA2, P16/CDKN2, EXT1, EXT2, PTEN/MMAC1, ATM, and TP73 genes. The genomic DNA target elements are produced by selecting genomic DNA clones from a human genomic library that map to the loci for these tumor suppressor genes. This selection is done by the preparation of PCR primer pairs from the loci or genes and subsequent library screening to identify the clones. In this embodiment, the clones for the tumor suppressor loci can be about 20 kb to 250 kb, and are preferably about 50 kb to about 200 kb in complexity.

(12) Utility of the Invention

The methods of the invention have significant utility in the fields of genetic research, human disease management, human disease clinical research, human disease drug development and pharmacogenomics, human genetic research, animal drug development, animal disease management, animal genetic research, and plant genetic research. In particular, by enabling more precise genetic detailing of suspected cancerous tissue, the invention will provide improved disease management through more tailored diagnosis and therapy selection. The methods can also be used to determine the presence of viruses, viral integration into chromosomes and expression of viral genes. The method can also be used to simultaneously detect human genomic DNA abnormalities, human gene expression and gene expression of bacterial genes.

The methods of the invention are particularly useful for genomic disease management of cancer and other disease. For example, the methods are useful for categorizing genotype and phenotype of cancer, including those of the breast, prostate, lung (small cell and non-small cell), ovary, cervix, kidney, head and neck, pancreas, stomach, brain, soft tissue and skin, and of various blood or lymphatic system cancers such as leukemias and lymphomas. Once the tumor tissue genotype and phenotype are categorized by the method of the invention, the physician can combine this data with other clinical data to determine diagnosis, prognosis, therapy and predict response to therapy.

The capabilities provided by the multi-color methods of the invention enable rapid comparative testing in drug development. For example, a cancer cell line can be dosed with a putative drug compound and at desired time intervals thereafter a cell sample can be removed. Each of the removed cell samples, for example, collected at time 0, 10, 20 and 30 hours after dosing, is treated to extract nucleic acids, which are then each labeled with a separate fluor. The four populations are then applied to the array with appropriate reference. The time-tracked effects of the drug on expression and initial chromosome status are thus assessed. Chromosomal change generally occurs over longer time periods and is not expected to change in this example. The method also can be applied to assess drug efficacy in drug resistant cell lines, particularly as drug resistance can be caused by gene amplification.

EXAMPLES

The following examples are intended to be rherely illustrative of the invention and are not to be construed as limiting.

Example 1

(A) Procedures (i) Test array manufacture: Four inch x four inch chromium-coated plates (Nanofilm) were scored by U.S. Precision Glass Company (Elgin, Ill.), and the scoring marked 24 equally sized chips. A 180 target element microarray was made on each chip. Before nucleic acid deposition, the plate was washed consecutively with distilled water, isopropanol, methanol and distilled water, allowed to dry and equilibrated to room temperature. The microarray was deposited centrally in each chip and occupied about 5 mm×6 mm of chip surface. The microarray was made using a computer-controlled, single needle fluid deposition robot supplied by New Precision Technologies (Northbrook, Ill.). The robot was modified by addition of a laser-based Z-axis controller, a pressure regulatable nitrogen gas line hooked to the deposition pin and a platen sized to hold twelve, 4"×4"plates. The robot used multiple deposition pins, each a 33 gauge, one-inch long steel capillary syringe needle linked to a Luer lock syringe tip from EFD. The capillary pins were each loaded with a different genomic DNA by loading into the Luer lock portion of the needle. The needle was changed manually after deposition of each target element on all chips on the platen. The microarray was made with approximately 400 micron spacing between target element centers in both the X and Y directions.

The robot was controlled with computer software provided with the robot, which was modified to bring the capillary pin into contact with the chip surface and, at the contact moment, to apply a microburst of nitrogen pressure to the top of the pin. The contact and microburst period was about 10 milliseconds per target element. The gas pressure was about 1 psi and was regulated manually, as necessary, to force sufficient amounts of the viscous genomic DNA out of the pin. The control conditions were set to deposit about 0.3 nl of 1 µg/µl nucleic acid in 100 mm NaOH per spot. The deposited elements were approximately round, with variations noticeable under microscope examination after DAPI staining. The spot size also varied with the viscosity of the DNA. Individual chips were separated manually.

The microarray comprised spots with genomic DNA from 31 human putative amplified gene loci, one spot of total human genomic DNA, three control spots of pooled genomic DNA, each spot a pool of equal amounts of genomic DNA for ten of these oncogene loci, and one spot of lambda phage DNA. These thirty-six spots were replicated five times each on the microarray to produce the one hundred-eighty spot microarray. The 31 human putative amplified gene loci are listed below, and were genomic human DNA inserted into BAC, PAC or PI cloning vectors. Each of the genomic DNA for these loci was produced with DNA of a single BAC, PAC or PI clone, although the individual insert sizes were not uniform. These BAC clones were obtained by screening the available genomic libraries with a primer sequence for each locus, as follows:

| GENE LOCUS | CLONE NO. | LIBRARY SOURCE[1] |
|---|---|---|
| MYCL1 | RMC01P052 | UCSF |
| FGR | RMC01P057 | UCSF |
| REL | BAC-274-P9 | GS |
| N-MYC | PAC-254-N16 | GS |
| RAF1 | BAC-98-L2 | GS |
| PIK3CA | PAC-97-816 | GS |
| PDGFRA | BAC-619-M20 | GS |
| MYB | BAC-268-N4 | GS |

-continued

| GENE LOCUS | CLONE NO. | LIBRARY SOURCE[1] |
|---|---|---|
| EGFR | BAC-246-M20 | GS |
| MET | BAC-54-J7 | RG |
| FLG | BAC-566-K20 | GS |
| C-MYC | P1-469 | GS |
| ABL | PAC-763-A4 | RG |
| BEK | BAC-126-B28 | GS |
| HRAS1 | BAC-137-C7 | GS |
| BCL1 | PAC-128-18 | GS |
| INT2 | BAC-36-F16 | GS |
| KRAS | BAC-490-C21 | GS |
| WNT1 | BAC-400-H17 | GS |
| GLI | RMC12P001 | UCSF |
| CDK4 | BAC-561-N1 | GS |
| MDM2 | BAC-82-N15 | GS |
| AKT1 | BAC-466-A19 | GS |
| FES | P1I-2298 | GS |
| HER2 | P1-506 | GS |
| YES1 | BAC-8-P19 | GS |
| JUNB | BAC-104-C10 | GS |
| 20 q 13.2 | BAC-97 | GS |
| PDGFB | RMC22P003 | UCSF |
| AR | PAC-1097-P11 | RG |

[1]GS is Genome systems; RG is Research Genetics; UCSF is the LBL/UCSF Resource for Molecular Cytogenetics, University of California, San Francisco, Cancer Center. The clone number for each locus is shown. Human insert sizes ranged from about 60 kb to about 212 kb; not all inserts were measured. Chromosome location for each is in TABLE 2 above.

(ii) Tissue extractions and labeling: For each of SJSA-1 and Colo 320 cell lines, obtained from ATCC, the cells were centrifuged at 7,000 rpm at 4° C. to produce cell pellets. Supernatant was discarded. The pellets were resuspended in Solution #2 of DNA Extraction Kit from Stratagene. The pellets were homogenized using a mechanical homogenizer at medium setting. Pronase was added to produce a pronase concentration of 100 µg/ml in each tube. Tubes were incubated with shaking at 60° C. for one hour. Tubes were placed on ice for 10 minutes. Stratagene DNA Extraction Kit Solution #3 was added and the tubes again placed on ice for 5 minutes. Tubes were centrifuged for 15 minutes at 8,000 rpm at 40° C. to pellet the protein precipitate. The supernatant was decanted. RNase was added to the supernatant to produce an Rnase concentration of 20 µg/ml and the supernatant incubated at 37° C. for 15 minutes. Two times the volume of ethanol was added and then centrifuged for 15 minutes at 10,000 rpm. Supernatant was decanted. The DNA pellets were dried under vacuum with a Speed Vac. The DNA pellets were resuspended in water and 995 µl of 50 mM sodium hydroxide added.

Cy-5 dUPT, from Amersham (Arlington Heights, Ill.) and a fluorescein labeled dCTP, produced according to Cruickshank, was used in nick translation to label the extracted DNA. The nick translation of Cy-5 dUPT for SJSA-1 incorporation used a standard protocol with a Promega (Madison, Wis.) nick translation kit. For Colo 320, 10 µl of nick translation enzyme and 5 µl of nick translation buffer (both from Vysis, Inc.) were mixed with 1 µg of extracted Colo 320 DNA, 4 µl each of dATP, dGTP and dTTP, 1 µl of dCTP, 2 µl of fluorescein dCTP, produced according to Cruickshank, and sufficient water to produce 50 µl of solution. The mix was incubated at 37° C. for 30 minutes. The enzyme was heat inactivated by heating at 80° C. for 10 minutes. The solution was G-25 Spin Column purified and the labeled probe dried with Speed Vac. for 40 minutes.

(iii) Hybridization: The nick translated DNA's (415 ng each), reference DNA (415 ng SpectrumOrange Total Human DNA (Vysis, Inc.), and Cot-1 DNA (100 µg), (LTI, Bethesda, Md.) were mixed with about 15 µl LSI Hybridization Buffer, (Vysis, Inc.), to produce 25, µl of hybridization mix. The hybridization mix was pipetted onto the chip contained in a chip holder shown in FIG. 1. The chip was glued in place in the holder using RTV 103 silicone rubber sealant (GE, Waterford, N.Y.). The probe clip 33 of FIG. 1 was applied as described above. The holder was then incubated at 37° C. overnight in an enclosed moisture chamber. After hybridization, the probe clip was removed and the chip washed with 2×SSC at room temperature for 5 minutes, the 2×SSC and 50% formamide at 40° C. for 30 minutes, and then 2×SSC at room temperature for 10 minutes. The washed chips were dried at room temperature in the dark. Ten µl of GEL/Mount™ and DAPI were added and an 18 mm×18 mm glass cover clip was placed over the array in the holder.

(iv) Image Capturing and Analysis: A bread-board imaging apparatus of Che was used to capture large field images of the hybridized array through the array window, without removal of the probe clip or cover slip. The bread-board image included a dual filter wheel (LudI) and single band pass filters (Chroma Technology, Battleboro, Vt.) for each of DAPI, fluorescein, SpectrumOrange and Cy5 were used for excitation and emission. Image data was processed using a Macintosh computer running algorithms that carried out the following steps: (1) Each target element spot is located from the DAPI image and assigned its grid location; (2) fluorescent intensities for each fluor at each spot are determined; (3) fluorescent ratios, by mode, median and mass, are calculated for each spot; (4) exclusion criteria based on spot size and intensity threshold; (5) composite images are produced and displayed on a computer monitor; (6) displayed images include white circles drawn around each spot and number of grid location; (7) printing capability for conventional computer-based printers; and (8) raw and processed data and image storage.

(B) Results

The fluorescence ratio for the Colo 320 compared to reference is shown in Table 3. As Table 3 indicates, the oncogene CMYC was amplified 32 fold in the Colo 320 cells. This compares to the known amplification of CMYC in Colo 320 of 29±6 fold (calculated from average of published data). A pseudo-colored composite image of the hybridization results showed significant color intensity for the CMYC elements, which also indicated amplification of the CMYC locus. Table 4 shows the fluorescent ratio analysis results for the SJSA-1 cells compared to reference. Table 4 shows the GLI (9.4 fold), MDM2 (7.5 fold) and CDK4/SAS (12.1 fold) loci are each amplified in SJSA-1 cells. A pseudo-colored composite image of the hybridization results showed significant color intensity for the GLI, MDM2 and CDK4/SAS elements, also indicating amplification. Table 5 shows the fluorescent ratio of the Colo 320 signal compared to the SJSA-1 signal for most targets is around 1. However, the low ratio of the GLI (0.12), MDM2 (0.13) and CDK4/SAS (0.09) indicates these gene loci were amplified in SJSA-1 cells relative to the Colo 320 cells. The high ratio of target CMYC (40) indicates the CMYC amplification in the Colo 320 cells. The gene amplification observed with three probes (two sample probes and one reference probe) hybridized simultaneously to one chip was similar to that obtained by separate hybridizations of the SJSA-1 and Colo 320 DNAs onto separate chips. (Subsequent to data collection, it was learned that the clone for the AKT2 locus was not correctly mapped. The data shown in Tables 3, 4 and 5 and in FIG. 2(a) through 2(h) for the AKT-2 target element are, thus, not meaningful.)

This Example 1 is the first demonstration known to the applicants of a comparative hybridization of more than two separately-labeled nucleic acid populations to the same array. These results demonstrate the simultaneous hybridization of three separately-labeled nucleic acid populations to a microarray to detect status of tissue nucleic acids.

TABLE 3

Test/Reference ratio analysis for the hybridization results of Example 1.
CMYC amplification in Colo 320 cells was observed.

| | | | Norm. Ratio: (by mode) | | (by median) | | (by mass) | | |
|---|---|---|---|---|---|---|---|---|---|
| Tgt. | Name | # | (Mean Cu) | | (Mean Cu) | | (Mean Cu) | | CorrC. |
| 1 | THD | 5 | ( 0.96 | 4%) | ( 1.04 | 3%) | ( 1.02 | 3%) | 0.951 |
| 2 | Lamb | 5 | ( 1.99 | 23%) | ( 2.47 | 13%) | ( 2.01 | 36%) | 0.446 |
| 3 | PDGFB | 5 | ( 0.81 | 11%) | ( 0.96 | 3%) | ( 0.96 | 3%) | 0.934 |
| 4 | EGFR | 5 | ( 0.83 | 12%) | ( 0.97 | 3%) | ( 0.94 | 3%) | 0.880 |
| 5 | PDGFRA | 5 | ( 0.68 | 4%) | ( 0.86 | 2%) | ( 0.83 | 2%) | 0.969 |
| 6 | MYB | 5 | ( 0.68 | 12%) | ( 0.75 | 6%) | ( 0.75 | 4%) | 0.941 |
| 7 | WNT 1 | 5 | ( 1.21 | 6%) | ( 1.29 | 3%) | ( 1.29 | 3%) | 0.973 |
| 8 | HRAS 1 | 5 | ( 1.48 | 9%) | ( 1.70 | 5%) | ( 1.65 | 4%) | 0.961 |
| 9 | MET | 5 | ( 0.80 | 15%) | ( 0.91 | 2%) | ( 0.90 | 3%) | 0.940 |
| 10 | BEK | 5 | ( 0.61 | 5%) | ( 0.77 | 14%) | ( 0.75 | 10%) | 0.943 |
| 11 | HER2 | 5 | ( 1.11 | 10%) | ( 1.22 | 3%) | ( 1.16 | 1%) | 0.956 |
| 12 | BCL 1 | 5 | ( 0.68 | 8%) | ( 0.75 | 4%) | ( 0.75 | 3%) | 0.961 |
| 13 | YES 1 | 5 | ( 0.85 | 3%) | ( 0.94 | 1%) | ( 0.93 | 1%) | 0.970 |
| 14 | RAF1 | 5 | ( 0.91 | 28%) | ( 1.09 | 2%) | ( 0.99 | 4%) | 0.931 |
| 15 | GLI | 5 | ( 1.04 | 7%) | ( 1.15 | 2%) | ( 1.16 | 3%) | 0.949 |
| 16 | MDM2 | 5 | ( 0.88 | 4%) | ( 0.97 | 3%) | ( 0.98 | 3%) | 0.968 |
| 17 | C-MYC | 5 | (28.74 | 6%) | (33.37 | 4%) | (32.30 | 2%) | 0.976 |
| 18 | 20Q13.2 | 5 | ( 0.77 | 6%) | ( 0.88 | 5%) | ( 0.86 | 3%) | 0.976 |
| 19 | REL | 5 | ( 0.97 | 2%) | ( 1.07 | 2%) | ( 1.04 | 2%) | 0.946 |
| 20 | MYCL1 | 5 | ( 0.99 | 9%) | ( 1.14 | 5%) | ( 1.09 | 4%) | 0.957 |
| 21 | FGR | 5 | ( 0.92 | 21%) | ( 0.94 | 3%) | ( 0.93 | 2%) | 0.970 |
| 22 | FES | 5 | ( 0.87 | 7%) | ( 0.98 | 4%) | ( 0.96 | 4%) | 0.962 |
| 23 | ABL | 5 | ( 1.12 | 10%) | ( 1.33 | 6%) | ( 1.25 | 1%) | 0.947 |
| 24 | INT2 | 5 | ( 0.72 | 4%) | ( 0.86 | 4%) | ( 0.84 | 3%) | 0.952 |
| 25 | PIK3CA | 5 | ( 0.83 | 11%) | ( 0.89 | 3%) | ( 0.87 | 7%) | 0.952 |

TABLE 3-continued

Test/Reference ratio analysis for the hybridization results of Example 1.
CMYC amplification in Colo 320 cells was observed.

| | | | Norm. Ratio: (by mode) | | (by median) | | (by mass) | | |
|---|---|---|---|---|---|---|---|---|---|
| Tgt. | Name | # | (Mean Cu) | | (Mean Cu) | | (Mean Cu) | | CorrC. |
| 26 | N-MYC | 5 | ( 1.02 | 5%) | ( 1.13 | 2%) | ( 1.12 | 2%) | 0.792 |
| 27 | AKT2 | 5 | ( 1.15 | 7%) | ( 1.21 | 4%) | ( 1.22 | 4%) | 0.964 |
| 28 | FLG | 5 | ( 1.03 | 8%) | ( 1.12 | 5%) | ( 1.12 | 4%) | 0.913 |
| 29 | JUNB | 5 | ( 0.92 | 4%) | ( 0.99 | 1%) | ( 0.97 | 1%) | 0.834 |
| 30 | AKT1 | 5 | ( 1.01 | 2%) | ( 1.06 | 4%) | ( 1.03 | 2%) | 0.906 |
| 31 | KRAS | 5 | ( 0.90 | 11%) | ( 1.02 | 6%) | ( 1.00 | 6%) | 0.965 |
| 32 | CDK4 | 5 | ( 1.02 | 5%) | ( 1.17 | 2%) | ( 1.12 | 2%) | 0.968 |
| 33 | A.R | 5 | ( 0.78 | 4%) | ( 0.85 | 2%) | ( 0.84 | 3%) | 0.961 |
| 34 | c1 | 5 | ( 0.96 | 9%) | ( 1.12 | 7%) | ( 1.10 | 7%) | 0.852 |
| 35 | c2 | 5 | ( 4.94 | 22%) | ( 5.68 | 11%) | ( 5.27 | 9%) | 0.967 |
| 36 | c3 | 5 | ( 0.93 | 3%) | ( 1.01 | 2%) | ( 1.01 | 1%) | 0.976 |
| All | | 178 | | 9% | | 4% | | 4% | 0.928 |
| Normalizer | | | 0.40 | | 0.38 | | 0.37 | | |

TABLE 4

Test/Reference ratio analysis for the hybridization results to Example 1.
GLI, MDM2 and CDK4/SAS amplification in SJSA-1 cells was observed.

| | | | Norm. Ratio: (by mode) | | (by median) | | (by mass) | | |
|---|---|---|---|---|---|---|---|---|---|
| Tgt. | Name | # | (Mean Cu) | | (Mean Cu) | | (Mean Cu) | | CorrC. |
| 1 | THD | 5 | ( 1.39 | 3%) | ( 1.15 | 2%) | ( 1.18 | 3%) | 0.976 |
| 2 | Lamb | 5 | ( 0.93 | 16%) | ( 0.65 | 18%) | ( 0.61 | 57%) | 0.563 |
| 3 | PDGFB | 5 | ( 1.21 | 8%) | ( 0.98 | 4%) | ( 0.99 | 2%) | 0.973 |
| 4 | EGFR | 5 | ( 1.40 | 16%) | ( 1.14 | 6%) | ( 1.15 | 4%) | 0.968 |
| 5 | PDGFRA | 5 | ( 1.25 | 3%) | ( 0.98 | 2%) | ( 0.99 | 2%) | 0.988 |
| 6 | MYB | 5 | ( 1.24 | 11%) | ( 1.01 | 6%) | ( 1.06 | 4%) | 0.980 |
| 7 | WNT 1 | 5 | ( 1.30 | 6%) | ( 1.04 | 4%) | ( 1.03 | 4%) | 0.976 |
| 8 | HRAS 1 | 5 | ( 1.15 | 7%) | ( 0.91 | 7%) | ( 0.93 | 5%) | 0.980 |
| 9 | MET | 5 | ( 1.31 | 6%) | ( 1.00 | 4%) | ( 1.03 | 3%) | 0.977 |
| 10 | BEK | 5 | ( 1.25 | 5%) | ( 0.92 | 6%) | ( 0.92 | 8%) | 0.941 |
| 11 | HER2 | 5 | ( 1.12 | 2%) | ( 0.85 | 1%) | ( 0.90 | 2%) | 0.976 |
| 12 | BCL 1 | 5 | ( 2.49 | 4%) | ( 1.94 | 4%) | ( 1.96 | 3%) | 0.987 |
| 13 | YES 1 | 5 | ( 1.32 | 2%) | ( 1.09 | 1%) | ( 1.08 | 1%) | 0.988 |
| 14 | RAF1 | 5 | ( 1.20 | 10%) | ( 0.92 | 4%) | ( 1.01 | 1%) | 0.969 |
| 15 | GLI | 5 | ( 11.55 | 4%) | ( 9.18 | 2%) | ( 9.39 | 3%) | 0.982 |
| 16 | MDM2 | 5 | ( 10.21 | 11%) | ( 7.39 | 12%) | ( 7.51 | 10%) | 0.976 |
| 17 | C-MYC | 5 | ( 1.03 | 4%) | ( 0.81 | 2%) | ( 0.81 | 2%) | 0.984 |
| 18 | 20Q13.2 | 5 | ( 1.14 | 8%) | ( 0.98 | 3%) | ( 0.99 | 2%) | 0.983 |
| 19 | REL | 5 | ( 1.27 | 2%) | ( 1.06 | 2%) | ( 0.99 | 13%) | 0.821 |
| 20 | MYCL1 | 5 | ( 1.40 | 4%) | ( 1.09 | 3%) | ( 1.13 | 1%) | 0.987 |
| 21 | FGR | 5 | ( 1.23 | 5%) | ( 0.97 | 3%) | ( 0.99 | 3%) | 0.986 |
| 22 | FES | 5 | ( 1.19 | 2%) | ( 0.95 | 2%) | ( 0.94 | 2%) | 0.979 |
| 23 | ABL | 5 | ( 0.92 | 12%) | ( 0.67 | 16%) | ( 0.71 | 10%) | 0.968 |
| 24 | INT2 | 5 | ( 1.78 | 4%) | ( 1.44 | 2%) | ( 1.50 | 2%) | 0.980 |
| 25 | PIK3CA | 5 | ( 1.03 | 5%) | ( 0.88 | 5%) | ( 0.85 | 7%) | 0.745 |
| 26 | N-MYC | 5 | ( 1.47 | 5%) | ( 1.24 | 2%) | ( 1.16 | 1%) | 0.987 |
| 27 | AKT2 | 5 | ( 1.23 | 6%) | ( 1.01 | 3%) | ( 1.03 | 3%) | 0.968 |
| 28 | FLG | 5 | ( 1.66 | 5%) | ( 1.35 | 1%) | ( 1.35 | 1%) | 0.956 |
| 29 | JUNB | 5 | ( 1.26 | 4%) | ( 1.01 | 1%) | ( 1.03 | 3%) | 0.949 |
| 30 | AKT1 | 5 | ( 1.11 | 2%) | ( 0.91 | 2%) | ( 0.92 | 3%) | 0.972 |
| 31 | KRAS | 5 | ( 1.23 | 11%) | ( 1.05 | 2%) | ( 1.06 | 1%) | 0.989 |
| 32 | CDK4 | 5 | (15.46 | 5%) | (11.69 | 6%) | (12.06 | 2%) | 0.976 |
| 33 | A.R | 5 | ( 0.98 | 3%) | ( 0.77 | 2%) | ( 0.77 | 2%) | 0.986 |
| 34 | cl | 5 | ( 1.44 | 9%) | ( 1.16 | 3%) | ( 1.19 | 2%) | 0.951 |
| 35 | c2 | 5 | ( 3.71 | 15%) | ( 2.68 | 6%) | ( 3.01 | 5%) | 0.978 |
| 36 | c3 | 5 | ( 4.09 | 2%) | ( 3.29 | 3%) | ( 3.33 | 2%) | 0.989 |
| All | | 176 | | 6% | | 4% | | 5% | 0.954 |
| Normalizer | | | 1.00 | | 1.20 | | 1.21 | | |

TABLE 5

Test/Reference ratio analysis for the hybridization results of Example 1.
GLI, MDM2 and CDK4/SAS amplification in SJSA-1 cells and CMYC amplification in Colo 320 cells were observed.

| Tgt. | Name | # | Norm. Ratio: (by mode) (Mean Cu) | | (by median) (Mean Cu) | | (by mass) (Mean Cu) | | CorrC. |
|---|---|---|---|---|---|---|---|---|---|
| 1 | THD | 5 | ( 0.92 | 6%) | ( 0.91 | 5%) | ( 0.88 | 4%) | 0.934 |
| 2 | Lamb | 5 | ( 3.24 | 0%) | ( 4.05 | 21%) | ( 4.39 | 52%) | 0.228 |
| 3 | PDGFB | 5 | ( 0.88 | 8%) | ( 0.98 | 5%) | ( 0.97 | 2%) | 0.904 |
| 4 | EGFR | 5 | ( 0.70 | 11%) | ( 0.88 | 7%) | ( 0.85 | 6%) | 0.856 |
| 5 | PDGFRA | 5 | ( 0.77 | 6%) | ( 0.91 | 13%) | ( 0.86 | 4%) | 0.963 |
| 6 | MYB | 5 | ( 0.62 | 3%) | ( 0.77 | 11%) | ( 0.72 | 3%) | 0.936 |
| 7 | WNT 1 | 5 | ( 1.14 | 8%) | ( 1.24 | 2%) | ( 1.28 | 8%) | 0.919 |
| 8 | HRAS 1 | 5 | ( 1.58 | 12%) | ( 1.96 | 12%) | ( 1.82 | 9%) | 0.944 |
| 9 | MET | 5 | ( 0.77 | 13%) | ( 0.91 | 6%) | ( 0.90 | 6%) | 0.928 |
| 10 | BEK | 5 | ( 1.22 | 94%) | ( 1.06 | 19%) | ( 0.90 | 19%) | 0.823 |
| 11 | HER2 | 5 | ( 1.26 | 11%) | ( 1.48 | 3%) | ( 1.31 | 2%) | 0.933 |
| 12 | BCL1 | 5 | ( 0.3 | 10%) | ( 1.38 | 8%) | ( 0.39 | 6%) | 0.951 |
| 13 | YES 1 | 5 | ( 0.83 | 4%) | ( 0.86 | 2%) | ( 0.88 | 2%) | 0.979 |
| 14 | RAF1 | 5 | ( 1.10 | 16%) | ( 1.22 | 2%) | ( 1.00 | 4%) | 0.902 |
| 15 | GLI | 5 | ( 0.12 | 2%) | ( 0.13 | 2%) | ( 0.12 | 3%) | 0.937 |
| 16 | MDM2 | 5 | ( 0.12 | 11%) | ( 0.14 | 17%) | ( 0.13 | 13%) | 0.960 |
| 17 | C-MYC | 5 | (36.47 | 6%) | (43.14 | 10%) | (40.45 | 2%) | 0.967 |
| 18 | 20Q13.2 | 5 | ( 0.88 | 6%) | ( 0.92 | 4%) | ( 0.89 | 2%) | 0.928 |
| 19 | REL | 5 | ( 0.98 | 6%) | ( 1.00 | 2%) | ( 1.02 | 2%) | 0.969 |
| 20 | MYCL1 | 5 | ( 0.93 | 13%) | ( 1.06 | 8%) | ( 0.98 | 5%) | 0.959 |
| 21 | FGR | 5 | ( 0.88 | 6%) | ( 0.96 | 5%) | ( 0.96 | 5%) | 0.949 |
| 22 | FES | 5 | ( 0.99 | 7%) | ( 1.04 | 5%) | ( 1.03 | 3%) | 0.948 |
| 23 | ABL | 5 | ( 2.00 | 39%) | ( 2.18 | 27%) | ( 1.99 | 30%) | 0.926 |
| 24 | INT2 | 5 | ( 0.57 | 8%) | ( 0.60 | 5%) | ( 0.57 | 5%) | 0.924 |
| 25 | PIK3CA | 5 | ( 1.44 | 70%) | ( 1.00 | 6%) | ( 1.05 | 4%) | 0.925 |
| 26 | N-MYC | 5 | ( 0.91 | 9%) | ( 1.01 | 1%) | ( 0.99 | 3%) | 0.959 |
| 27 | AKT2 | 5 | ( 1.15 | 9%) | ( 1.18 | 2%) | ( 1.20 | 2%) | 0.906 |
| 28 | FLG | 5 | ( 0.85 | 12%) | ( 0.83 | 4%) | ( 0.84 | 4%) | 0.865 |
| 29 | JUNB | 5 | ( 0.97 | 5%) | ( 0.98 | 3%) | ( 0.97 | 3%) | 0.918 |
| 30 | AKT1 | 5 | ( 1.21 | 6%) | ( 1.17 | 3%) | ( 1.15 | 2%) | 0.893 |
| 31 | KRAS | 5 | ( 0.91 | 9%) | ( 0.96 | 9%) | ( 0.96 | 7%) | 0.968 |
| 32 | CDK4 | 5 | ( 0.09 | 4%) | ( 0.11 | 9%) | ( 0.09 | 3%) | 0.960 |
| 33 | A.R | 5 | ( 1.00 | 6%) | ( 1.08 | 2%) | ( 1.12 | 1%) | 0.960 |
| 34 | c1 | 5 | ( 0.93 | 11%) | ( 0.99 | 5%) | ( 0.93 | 3%) | 0.824 |
| 35 | c2 | 5 | ( 2.68 | 18%) | ( 2.40 | 8%) | ( 1.78 | 5%) | 0.939 |
| 36 | c3 | 5 | ( 0.29 | 3%) | ( 0.31 | 5%) | ( 0.31 | 3%) | 0.966 |
| All | | 180 | | 13% | | 7% | | 7% | 0.954 |
| Normalizer | | | 0.31 | | 0.32 | | 0.30 | | |

Example 2

(A) Procedures (i) Array: The same 180 element microarray of Example 1 was used.

(ii) Tissue extraction and labeling: Two cell lines were used in this experiment, Colo 320 and K562, both from ATCC. Five million cells of each were spun down (1.5K for 10 min.) to pellet. After decanting, 100 μl RNase solution and 300 μl lysis solution were added to the pellet and the mixture were vortexed at high speed briefly. The mRNA for each cell line were isolated by nitrocellulose-polyT using the isolation protocol was provided by the manufacturer (Ambion, Tex.).

The isolated mRNA was ethanol precipitated and reverse transcribed in the presence of Cy-5-dCTP (Amersham) using conventional protocol and primered by random pN9 to produce the Cy-5 labeled cDNA probe, of which one-fifth was used for each hybridization assay (one million cell for each assay). DNA was isolated for each cell line with conventional phenol-chloroform extraction and labeled with nick translation in the presence of fluorescein dCTP as in Example 1 to produce the labeled gDNA.

(iii) Hybridization: Each hybridization was at total volume of 25 μl consisting of 15 μl LSI hybridization buffer (Vysis, Inc.), 200 ng cell line gDNA probe, 200 ng cell line cDNA probe, 200 ng SpectrumOrange Total Human Genomic DNA (Vysis, Inc.) as the reference, 20 μg salmon sperm DNA and 40 μg Cot-1 DNA. Hybridization was to microarrays in chip holders with probe chip as in Example 1, and was carried out at 42° C. in an enclosed moisture chamber for three days. For each cell line, the hybridization was duplicated on two chips. The overall process is shown below:

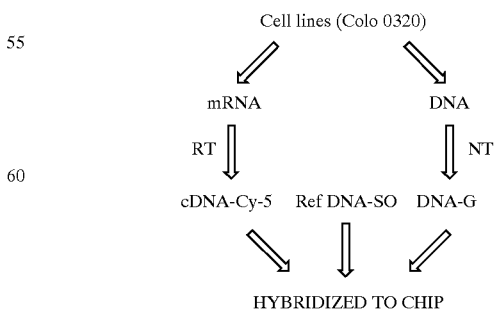

-continued

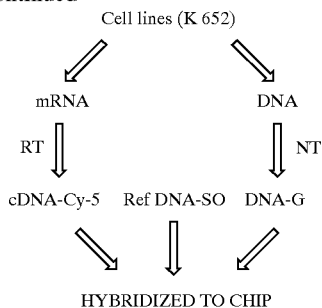

Cell lines (K 652)

HYBRIDIZED TO CHIP (iv) Imaging capturing and data analysis: Fluorescent images of hybridized chips were taken and analyzed, as in Example 1, with the breadboard dual-filter wheel imaging system of Che. Single-band pass filters were used for both excitation and emission. Images were analyzed with the same software as in Example 1.

(B) Results

General description of figures: Data are presented as scatter plots and/or bar graphs. The scatter plots, with each point corresponding to a particular target clone, serve as statistical representation of data sets. The information for any given target clone can be extracted from the bar graphs.

(i) Signal Intensitv: The intensities of background corrected signal for the genes in the microarray were comparable between tissue cDNA (average of 165 counts for 10 seconds exposure) and tissue gDNA (average of 187 counts for 10s exposure). Background associated with cDNA detection was higher, 132 counts as compared to 73 counts for gDNA. For both cDNA and gDNA, even the weakest signals were well above background (S/B>1) with 60 seconds exposure, provided that enough probe was deposited on the chip.

(ii) Data reliability: FIG. 2(a) shows the correlation of genomic DNA hybridization data obtained from two hybridizations for each of the cell lines. Linear regression correlation of the data for Colo 320 and K562 are 0.9963 and 0.9999, respectively, indicating high reliability of the data. As expected, the ratios of the tissue gDNA over human reference gDNA formed a cluster for a majority of the target element genes (around one after normalization). Ratios that were distant from the cluster indicate gene amplifications in the cell lines for the corresponding genes (CMYC in Colo 320 and ABL in K562). It is interesting to note that for both cell lines that were tested, the "normal" cluster spans a ratio range from 0.5 to 1.5. Within this range, the values of the ratio were highly reproducible between experiments and they were distributed such that it was believed unreliable to identify any particular gene within this cluster as deleted or amplified.

FIG. 2(b) shows the reliability of gene expression hybridization data obtained from two hybridizations for each cell line. Linear regression correlation of the two sets of data for Colo 320 and K562 were 0.9989 and 0.9790, respectively.

(iii) Assay MultiDlexing: FIG. 2(c) (for K562 cell line) and FIG. 2(d) (for Colo 320 cell line) demonstrate the assay multiplexing achieved with the new assay format. With a separate genomic DNA assay, one could detect only the genomic copy numbers (relative to human reference) of the target sequences (green bars). With an expression cDNA assay, one could only detect the expression profile (some equivalence of red bars). With the method of the invention, the genomic and expression data were acquired simultaneously.

(iv) Use of normal human total gDNA as reference for expression assay: Normally, because of lack of a "universal" or "normal" reference, the expression levels of two samples can be compared reliably only when the expression assays for the two samples are performed on the same chip in separate assays. Example 2 used total normal human gDNA as the reference nucleic acid for expression assay. When using the tissue cDNA and reference gDNA labeled with fluorochromes of different color, after hybridization, the fluorescent intensity ratio of the two colors should reflect the initial concentration ratio of the cDNA and reference gDNA in the probe solution. If a particular reference gDNA is readily available and its copy numbers of gene specific sequence do not change (i.e., are "stable") or varies only negligibly, then it can be used as a universal reference for all expression assays. The expression profile can be expressed as the ratio of cDNA over reference gDNA as shown in FIG. 2(e). This ratio profile is sample and sample only dependent. In other words, if two expression assays of the same sample are carried out in two separate hybridization on two different chips comprising the same array, the expression profiles obtained from the two assays should differ only by a scaling factor which is constant for all targets. Different samples will exhibit different expression profiles (expressed as ratio to reference genomic DNA). Comparison of FIGS. 2(b) and 2(e) show that the expression profiles are indeed sample and sample only dependent. With the use of total human genomic DNA as a reference for expression analysis in the methods of the invention, the expression profiles of different samples can be compared even if the assays are carries out separately and independently.

Figure 2F:
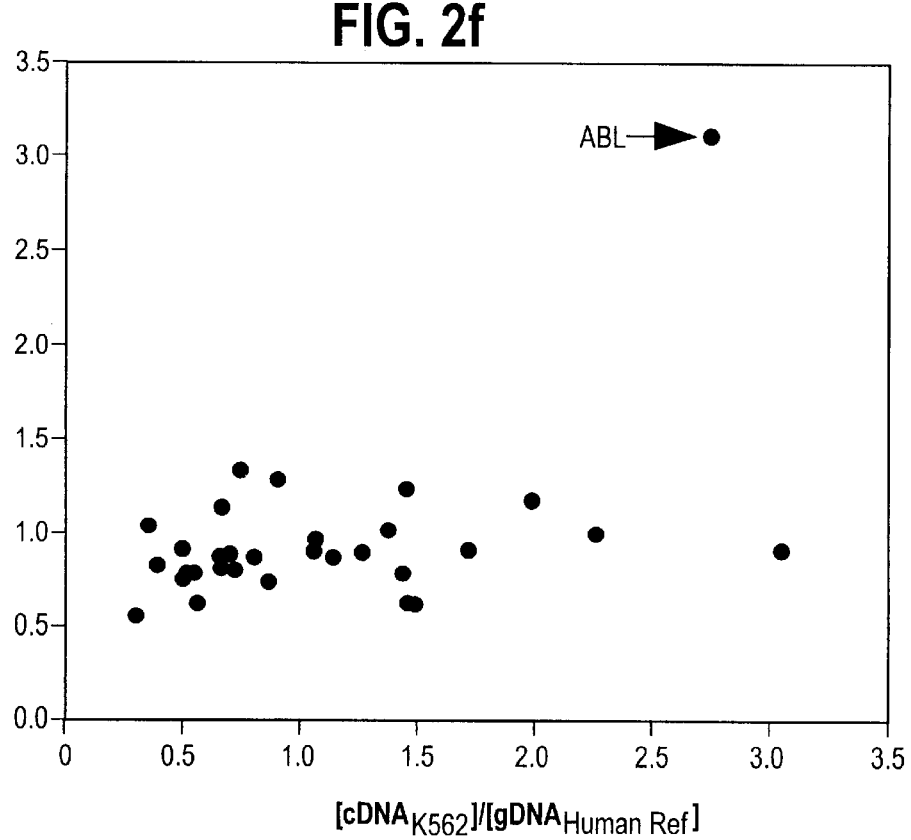
Figure 2G:
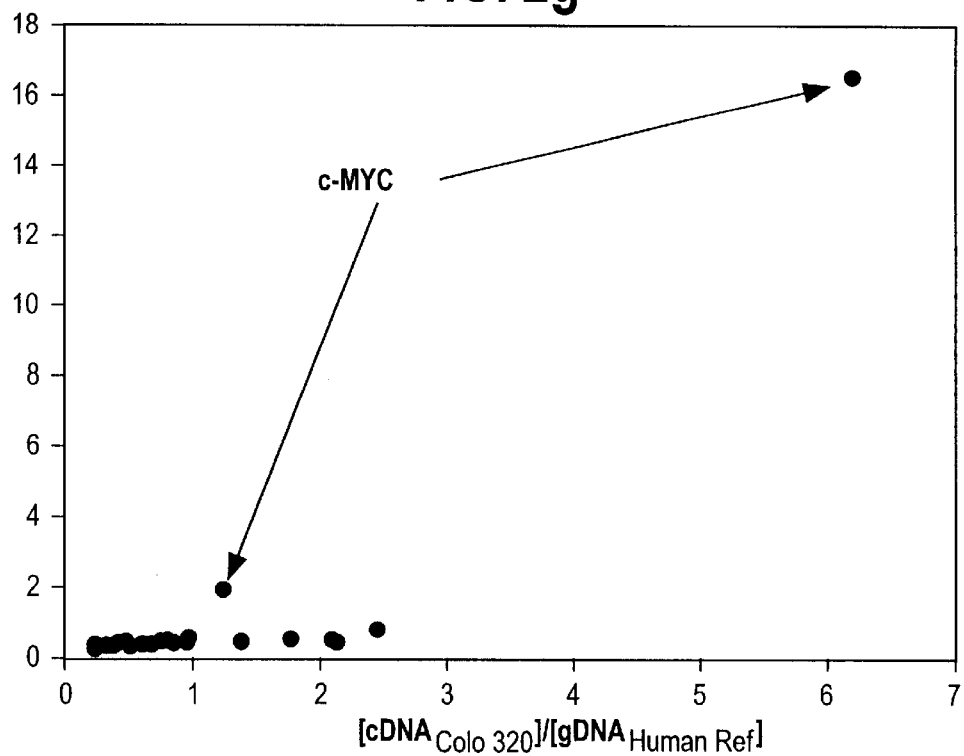

(v.) Correlating genomic amplification to gene over-expression: FIG. 2(f) and 2(g) are plots of genomic copy number vs cDNA (both relative to reference genomic DNA) for K562 and Colo 320 cell lines, respectively.

As expected, within a cell line, except for the amplified genes, the expression levels for the rest of the genes analyzed varied widely while their genomic copy number maintains relatively constant. As shown in FIG. 2(e), in both cell lines, for some genes, such as JUNB, HRAS1, GLI, the cDNAs are more abundant while for others, such as PDGFRA, BEK, MDM2, the cDNAs are less abundant. Significantly, for C-MYC and ABL, the expression levels are very different for the two cell lines and the trend is in accordance with their amplification at the genomic level. The over-expression of C-MYC in Colo 320 and ABL in K562 can be attributed to gene amplification. FIG. 2(h) is the plot of "gene expression" ratio vs "gene copy number" ratio between the two cell lines. Interestingly, there was a remarkable correlation between the two quantities. (Linear regression results, Y=0.262x+0.724, correlation 0.985). In the graph, genes that are unamplified in both cell lines form a cluster, while genes that are unequally amplified in the two cell lines are separated apart from the cluster. This graph, or more generally, the simultaneous genomic and expression assay, facilitates reliable attribution of over-or under-expression to gene amplification or deletion.

The specification of this application is not intended to be limiting as to the scope of the invention. All patents, patent applications and published references cited herein are hereby incorporated by reference. The scope of the invention is determined by the following claims, including any and all equivalents thereof.

We claim:

1. A method for simultaneous detection of gene expression and chromosomal abnormality in a tissue sample comprising:

(a) providing an array of nucleic acid target elements attached to a solid support wherein the nucleic acid target elements comprise polynucleotide sequences substantially complementary under preselected hybridization conditions to nucleic acids indicative of gene expression and indicative of chromosomal sequence of a tissue sample;

(b) providing at least three labeled nucleic acid populations:

(i) a mRNA or cDNA population labeled with a first marker and derived from the tissue sample, (ii) a chromosomal DNA population labeled with a second marker and derived from the tissue sample, and (iii) at least one reference nucleic acid population labeled with a third marker;

(c) contacting the array with the labeled nucleic acid populations under hybridization conditions; and (d) detecting presence and intensity of each of the first, second and third markers on at least two target elements.

2. The method of claim 1 wherein the target elements comprise genomic DNA.

3. The method of claim 1 wherein the target elements comprise cDNA.

4. The method of claim 1 wherein the tissue sample is from a human.

5. The method of claim 1 wherein the array comprises cDNA and genomic DNA target elements.

6. The method of claim 1 wherein the array comprises target elements at a density in the range of 100 to 10,000 target elements per square centimeter.

7. The method of claim 1 wherein the first, second and third markers each comprise a different fluorescent label.

8. The method of claim 1 further comprising processing data from the detecting step (c) in a programmed computer, storing raw and processed data in a database and displaying raw and processed data.

9. The method of claim 1 further comprising addition of unlabeled blocking nucleic acid.

10. The method of claim 4 further comprising use of data derived from the method in selection of therapy for a human.

11. The method of claim 1 further comprising determining fluorescent ratios at each target element (i) between the first and third markers and (ii) between the second and third markers.

12. The method of claim 1 wherein the tissue comprises a cell line sample.

13. The method of claim 1 wherein the tissue sample comprises one cell.

14. The method of claim 1 wherein the tissue sample comprises a human tumor sample.

15. The method of claim 1 wherein the tissue sample comprises blood cells.

16. The method of claim 2 wherein the genomic DNA comprises human genomic DNA having a complexity in a range of 20 kb to 250 kb.

17. The method of claim 3 wherein the cDNA comprises cDNA having a complexity in a range of 100 bp to 5,000 bp.

18. The method of claim 1 wherein the target nucleic acid elements comprise at least one peptide nucleic acid.

19. The method of claim 1 wherein the method is performed in a mesoscale device.

20. A method for simultaneous detection of gene expression and chromosomal abnormality in a tissue sample comprising:

(a) providing an array of nucleic acid target elements comprising genomic DNA attached to a solid support wherein the nucleic acid target elements comprise polynucleotide sequences substantially complementary under preselected hybridization conditions to nucleic acids indicative of gene expression and indicative of chromosomal sequence of a tissue sample;

(b) providing at least three labeled nucleic acid populations:

(i) a mRNA or cDNA population labeled with a first fluorescent marker and derived from the tissue sample, (ii) a chromosomal DNA population labeled with a second fluorescent marker and derived from the tissue sample, and (iii) at least one reference nucleic acid population labeled with a third fluorescent marker;

(c) contacting the array with the labeled nucleic acid populations under hybridization conditions; and (d) detecting presence and intensity of each of the first, second and third fluorescent markers on at least two target elements.

21. The method of claim 20 wherein the array comprises at least 100 target elements on a planar surface of a substrate.

22. The method of claim 20 wherein the array comprises target elements at a density in the range of 100 to 10,000 target elements per square centimeter.

23. The method of claim 20 further comprising determining fluorescent ratios at each target element (i) between the first and third markers and (ii) between the second and third markers.

24. The method of claim 20 further comprising processing data from the detecting step (c) in a programmed computer, storing raw and processed data in a database and displaying raw and processed data.

25. The method of claim 20 further comprising addition of unlabeled blocking nucleic acid.

26. The method of claim 20 further comprising use of data from the method in selection of therapy for a human.

27. The method of claim 20 wherein the chromosomal DNA population is produced by a method comprising PCR.

28. The method of claim 20 wherein the tissue sample comprises one cell.

29. The method of claim 20 wherein the tissue sample comprises a human tumor sample.

30. The method of claim 20 wherein the tissue sample comprises blood cells.

31. The method of claim 20 wherein the tissue sample comprises a human blastomere cell or a human polar body.

32. The method of claim 20 wherein the tissue sample is produced by microdissection.

33. The method of claim 20 wherein the method is performed in a mesoscale device.

34. A method for simultaneous detection of gene expression and chromosomal abnormality in a tissue sample comprising:

(a) providing an array of nucleic acid target elements attached to a solid support wherein the nucleic acid target elements comprise polynucleotide sequences substantially complementary under preselected hybridization conditions to nucleic acids indicative of gene expression and indicative of chromosomal sequence of a tissue sample;

(b) providing at least three labeled nucleic acid populations:

(i) a mRNA or cDNA population labeled with a first fluorescent marker and derived from the tissue sample, (ii) a chromosomal DNA population labeled with a second fluorescent marker and derived from the tissue sample, and (iii) at least one reference nucleic acid population labeled with a third fluorescent marker;

(c) contacting the array with the labeled nucleic acid populations under hybridization conditions; and (d) detecting presence and intensity of each of the first, second and third fluorescent markers on at least two target elements.

35. The method of claim 34 wherein the target nucleic acid elements comprise oligomers in the range of 8 bp to about 100 bp.

36. The method of claim 34 wherein the array comprises at least 100 target elements.

37. The method of claim 34 wherein the array comprises target elements at a density in the range of 100 to 10,000 target elements per square centimeter.

38. The method of claim 34 further comprising determining fluorescent ratios at each target element (i) between the first and third markers and (ii) between the second and third markers.

39. The method of claim 34 further comprising processing data from the detecting step (c) in a programmed computer, storing raw and processed data in a database and displaying raw and processed data.

40. The method of claim 34 further comprising addition of unlabeled blocking nucleic acid.

41. The method of claim 34 further comprising use of data from the method in selection of a therapy for a human.

42. The method of claim 34 wherein the chromosomal DNA population is produced by a method comprising PCR.

43. The method of claim 34 wherein the tissue sample comprises one cell.

44. The method of claim 34 wherein the tissue sample comprises a human tumor sample.

45. The method of claim 34 wherein the tissue sample comprises blood cells.

46. The method of claim 34 wherein the tissue sample is produced by microdissection.

47. The method of claim 34 wherein the cDNA comprises cDNA having a complexity in a range of 100 bp to 5,000 bp.

48. The method of claim 34 wherein the target nucleic acid elements comprise at least one peptide nucleic acid.

49. The method of claim 34 wherein the method is performed in a mesoscale device.

50. The method of claim 1 wherein the target elements comprise polynucleotides in the range of 8 bp to about 100 bp.

51. The method of claim 4 wherein the tissue sample comprises bladder tissue.

52. The method of claim 4 wherein the tissue sample comprises lung tissue.

53. The method of claim 4 wherein the tissue sample comprises prostate tissue.

54. The method of claim 4 wherein the tissue sample comprises breast tissue.

55. The method of claim 4 wherein the tissue sample comprises esophageal tissue.

56. The method of claim 4 wherein the tissue sample comprises cervical tissue.

57. The method of claim 4 wherein the tissue sample comprises ovarian tissue.

58. The method of claim 4 wherein the tissue sample comprises colon tissue.

59. The method of claim 4 wherein the tissue sample comprises brain tissue.

60. The method of claim 4 wherein the tissue sample comprises stomach tissue.

61. The method of claim 4 wherein the tissue sample comprises skin tissue.

62. The method of claim 4 wherein the tissue sample comprises pancreas tissue.

63. The method of claim 4 wherein the tissue sample comprises a human blastomere.

64. The method of claim 4 wherein the tissue sample comprises a human polar body.

65. The method of claim 1 comprising use of at least two reference nucleic acid populations.

66. The method of claim 1 comprising use of at least four reference nucleic acid populations.

67. The method of claim 20 comprising use of at least two reference nucleic acid populations.

68. The method of claim 34 comprising use of at least two reference nucleic acid populations.

69. The method of claim 4 comprising use of at least two reference nucleic acid populations.

70. The method of claim 4 wherein the tissue sample comprises a cancer cell line.

71. The method of claim 20 wherein at least four separate fluorescently labeled nucleic acid populations are hybridized with the array.

72. The method of claim 20 wherein at least eight separate fluorescently labeled nucleic acid populations are hybridized with the array.

73. The method of claim 5 wherein at least four separate fluorescently labeled nucleic acid populations are hybridized with the array.

74. The method of claim 34 wherein at least four separate fluorescently labeled nucleic acid populations are hybridized with the array.

75. The method of claim 34 wherein at least eight separate fluorescently labeled nucleic acid populations are hybridized with the array.

76. The method of claim 8 which further comprises: displaying at least one chromosome ideogram with array data.

77. The method of claim 24 which further comprises: displaying at least one chromosome ideogram with array data.

78. The method of claim 40 which further comprises: displaying at least one chromosome ideogram with array data.

* * * * *